(12) United States Patent
Nagy et al.

(10) Patent No.: US 9,730,991 B2
(45) Date of Patent: Aug. 15, 2017

(54) LIVE ATTENUATED SHIGELLA VACCINE

(71) Applicant: EVELIQURE BIOTECHNOLOGIES GMBH, Vienna (AT)

(72) Inventors: Gábor Nagy, Sopron (HU); Tamás Henics, Vienna (AT); Valeria Szijártó, Vienna (AT); Eszter Nagy, Vienna (AT)

(73) Assignee: EVELIQURE BIOTECHNOLOGIES GMBH, Vienna (AT)

( * ) Notice: Subject to any disclaimer, the term of this patent is extended or adjusted under 35 U.S.C. 154(b) by 0 days.

(21) Appl. No.: 14/426,123

(22) PCT Filed: Sep. 5, 2013

(86) PCT No.: PCT/EP2013/068365
§ 371 (c)(1),
(2) Date: Mar. 4, 2015

(87) PCT Pub. No.: WO2014/037440
PCT Pub. Date: Mar. 13, 2014

(65) Prior Publication Data
US 2015/0246107 A1    Sep. 3, 2015

(30) Foreign Application Priority Data
Sep. 6, 2012 (EP) .................... 12183347

(51) Int. Cl.
*A61K 35/74* (2015.01)
*A61K 39/112* (2006.01)
*A61K 39/00* (2006.01)

(52) U.S. Cl.
CPC .......... *A61K 39/0283* (2013.01); *A61K 35/74* (2013.01); *A61K 2039/522* (2013.01); *A61K 2039/523* (2013.01); *A61K 2039/70* (2013.01)

(58) Field of Classification Search
None
See application file for complete search history.

(56) References Cited

U.S. PATENT DOCUMENTS 5,877,159 A * 3/1999 Powell .................. A61K 48/00
424/184.1

FOREIGN PATENT DOCUMENTS

| CN | 1315871 A | 10/2001 |
|---|---|---|
| WO | WO 00/04919 | 2/2000 |
| WO | WO 2011/044499 | 4/2011 |

OTHER PUBLICATIONS

Ranallo et al. FEMS Immunol Med Microbiol 47 (2006) 462-469.*
Buchrieser et al. Molecular Microbiology (2000) 38 (4) 760-771.*
Sharan et al. Nat. Protoc. 2009; 4(2):206-223.*
Phalipon, A. et al., "Shigella's ways of manipulating the host intestinal innate and adaptive immune system: a tool box for survival?", *Immunology and Cell Biology*, 85:119-129, 2007.
Picking, Wendy et al., "Identification of functional regions within invasion plasmid antigen C (IpaC) of Shigella flexneri", *Molecular Microbiology*, 39:100-111, 2001.
Teh, Min Yan et al., "Absence of O antigen suppresses Shigella flexneri IcsA autochaperone region mutations," *Microbiology*, 158:2835-2850, 2012.
M. Bernardini et al., "Parameters Underlying Successful Protection with Live Attenuated Mutants in Experimental Shigellosis", *Infection and Immunity*, 69:2:1072-1083, 2001.
J. Carter et al., "O-antigen Modal Chain Length in *Shigella flexneri* 2a is Growth-Regulated through RfaH-Mediated Transcriptional Control of the wzy gene", *Microbiology*, 153:3499-3507, 2007.
K. Datsenko et al., "One-step Inactivation of Chromosomal Genes in *Escherichia coli* K-12 Using PCR Products", *Proc. Natl. Acad. Sci.*, 97:12:6640-6645, 2000.
A. Guichon et al., "Structure-Function Analysis of the *Shigella* Virulence Factor IpaB", *Journal of Bacteriology*, 183:4:1269-1276, 2001.
M. Hong et al., "Effect of Mutations in *Shigella flexneri* Chromosomal and Plasmid-Encoded Lipopolysaccharide Genes on Invasion and Serum Resistance", *Molecular Microbiology*, 24:4:779-791,1997.
M. Hong et al. "Identification of Two *Shigella flexneri* Chromosomal Loci Involved in Intercellular Spreading", *Infection and Immunity*, 66:10:4700-4710, 1998.
K. Kotloff et al., "Global Burden of *Shigella* Infections: Implications for Vaccine Development and Implementation of Control Strategies", *Bulletin of the World Health Organization*, 77:8:651-666, 1999.
M. Levine et al., "Attenuated *Salmonella typhi* and *Shigella* as Live Oral Vaccines and as Live Vectors", *Behring Inst. Mitt.*, 98:120-123, 1997.
M. Levine et al., "Clinical Trials of *Shigella* Vaccines: Two Steps Forward and One Step Back on a Long, Hard Road", *Nat. Rev. Microbiol*, 5:7:540-553, 2007.
R. Ménard et al., "Nonpolar Mutagenesis of the ipa Genes Defines IpaB, IpaC, and IpaD, as Effectors of *Shigella flexneri* Entry into Epthelial Cells", *Journal of Bacteriology*, 175:18:5899-5906,1993.
G. Nagy et al., "Gently Rough: The Vaccine Potential of a *Salmonella enterica* Regulatory Lipopolysaccharide Mutant", *Journal of Infectious Diseases*, 198:1699-1706, 2008.
J. Nataro et al., "Diarrheagenic *Escherichia coli*", *Clinical Microbiology Reviews*, 11:1:142-201, 1998.
F. Noriega et al., "Strategy for Cross Protection among *Shigella flexneri* Serotypes", *Infection and Immunity*, 67:2:782-788, 1999.
F. Noriega et al., "Further Characterization of ΔaroA ΔvirG *Shigella flexneri* 2a Strain CVD 1203 as a Mucosal *Shigella* Vaccine and as a Live-Vector Vaccine for Delivering Antigens of Enterotoxigenic *Escherichia coli*", *Infection and Immunity*, 64:1:23-27, 1996.

(Continued)

*Primary Examiner* — Oluwatosin Ogunbiyi
(74) *Attorney, Agent, or Firm* — Seyfarth Shaw LLP

(57) ABSTRACT

A live attenuated *Shigella* vaccine, which is based on a rough *Shigella* strain lacking LPS O-antigen which is non-invasive through a mutation of the invasion plasmid, specifically for use in the immunoprophylaxis of a subject to prevent infectious diseases, preferably enteral disease, and a *Shigella* strain, which is a *S. flexneri* 2a strain with a deletion of the rfb F, ipa B and/or ipa C genes, as well as a recombinant plasmid vector based on a mutated *Shigella* invasion plasmid comprising a nucleotide sequence encoding at least one heterologous antigen, wherein the plasmid is mutated in at least one of the ipa B and/or ipa C genes.

29 Claims, 15 Drawing Sheets

(56) References Cited

OTHER PUBLICATIONS

Figure 3:
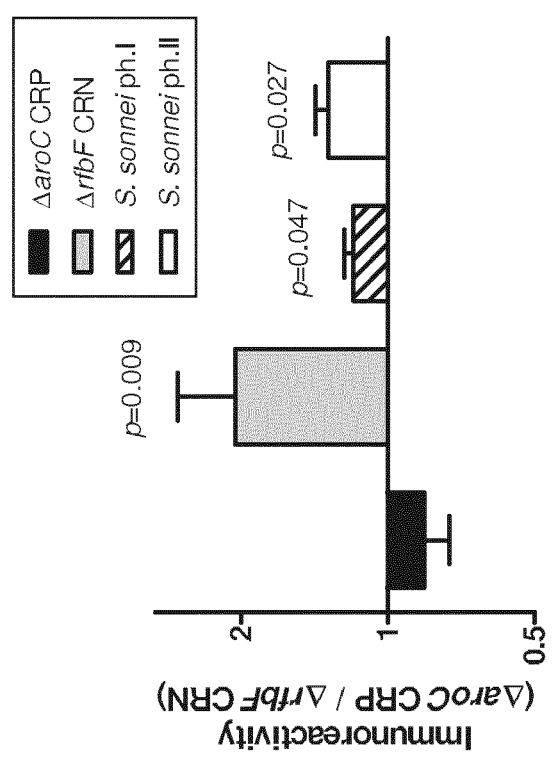

E. Oaks et al. "Serum Immune Response to *Shigella* Protein Antigens in Rhesus Monkeys and Humans Infected with *Shigella* spp.", *Infection and Immunity*, 53:1:57-63, 1986.
A. Taxt et al. "Heat-Stable Enterotoxin of Enterotoxigenic *Escherichia coli* as a Vaccine Target", *Infection and Immunity*, 78:5:1824-1831, 2010.
L. Van De Verg et al. "Antibody and Cytokine Responses in a Mouse Pulmonary Model of *Shigella flexneri* Serotype 2a Infection", *Infection and Immunity*, 63:5:1947-1954, 1995.
J. Wei, et al., "Complete Genome Sequence and Comparative Genomics of *Shigella flexneri* Serotype 2a Strain 2457T", *Infection and Immunity*, 71:5:2775-2786, 2003.
P. Wood et al., "Comparison of DNA Probes and the Sereny Test for Identification of Invasive *Shigella* and *Escherichia coli* Strains", *Journal of Clinical Microbiology*, 24:3:498-500, 1986.
F. Xu et al., "Immunogenicity of an HIV-1 gag DNA Vaccine Carried by Attenuated *Shigella*" *Vaccine*, 21:644-648, 2003.
W. Zhang et al. "Prevalence of Virulence Genes in *Escherichia coli* Strains Recently Isolated from Young Pigs with Diarrhea in the US", *Veterinary Microbiology*, 123:145-152, 2007.
J. Zheng et al., "Construction of a Novel *Shigella* Live-Vector Strain Co-Expressing CS3 and LTB/ STm of Enterotoxigenic *E.coli*", *World J Gastroenterol*, 11:22:3411-3418, 2005.
International Search Report, Int'l Appl. No. PCT/EP2013/068365, mailed Jul. 30, 2014.
Written Opinion of the International Searching Authority, Int'l Appl. No. PCT/EP2013/068365, mailed Jul. 30, 2014.
EP Search Report, EP Appl. No. 12183347.9, mailed Dec. 12, 2012.
EP Search Report, EP Appl. No. 12183347.9, mailed Mar. 28, 2013.
International Search Report, Int'l Appl. No. PCT/EP2013/068365, mailed Feb. 10, 2014.
Allaoui A. et al., "MxiD, an outer membrane protein necessary for the secretion of the Shigella flexneri Ipa invasins," *Mol Microbiol*, 7:59-68, 1993.
Blocker, A. et al., "Structure and compositon of the Shigella flexneri 'needle complex', a part of its type III secretion," *Mol Microbiol*, 39:652-663, 2001.
Jennison Amy v., "Shigella flexneri infection: pathogenesis and vaccine development," *FEMS Microbiology Reviews*, 28:1:43-58, 2004 (first published online Sep. 21, 2003).
Qadri et al., "Congo Red Binding and Salt Aggregation as Indicators of Virulence in *Shigella* Species," *J Clin Microbiol*, 26:1343-1348, 1988.
Tamano, K. et al., Supramolecular structure of the Shigella type III secretion machinery: the needle part is changeable in length and essential for delivery of effectors, *EMBO J*, 19:3876-3887, 2000.

\* cited by examiner

Fig. 1
a) 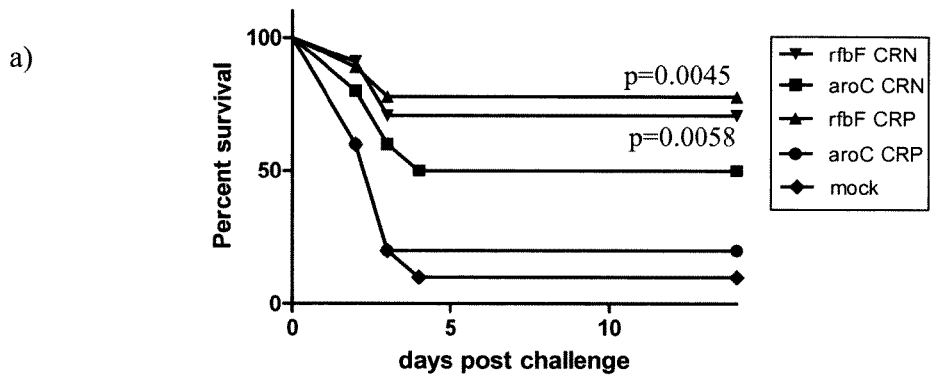
b) 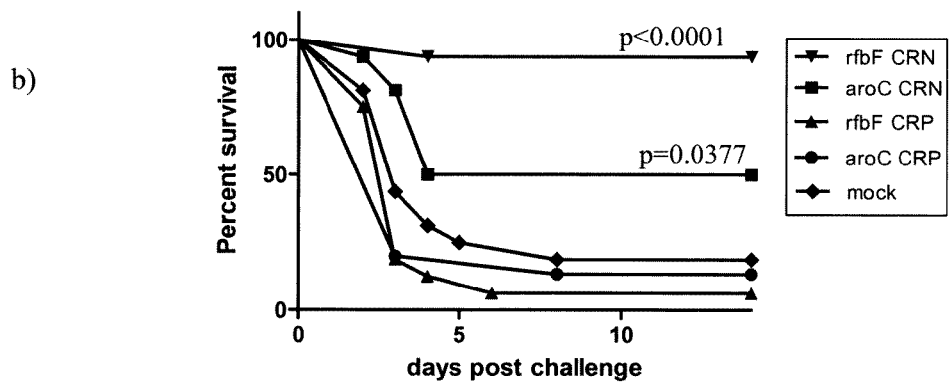
c) 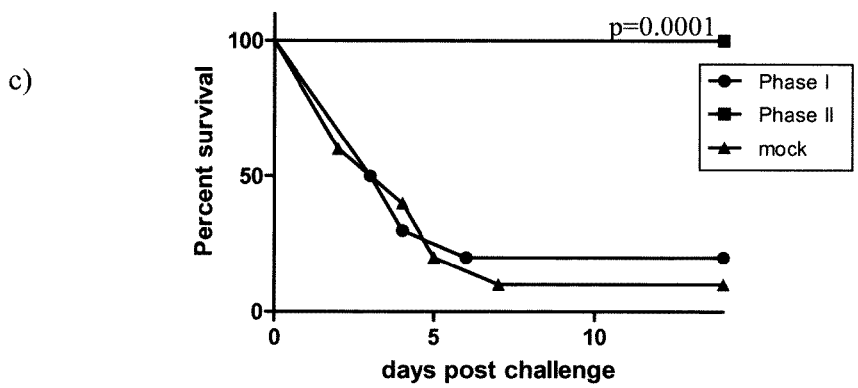

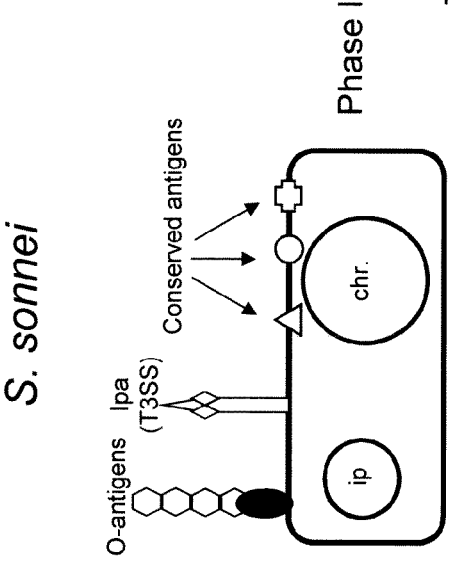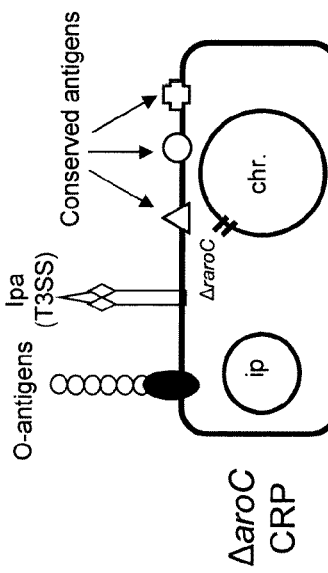
Fig. 2

Fig. 4

| Oligo-nucleotide | Function | Oligonucleotid sequence [a] |
|---|---|---|
| aroCpKD-F | Amplification of PCR product used for the allelic exchange of aroC | 5' CGC ACG GGC TGG CGC TCG GCT GCT GCA TCG TCG ATG GTG TTC C*GT GTA GGC TGG AGC TGC TTC* 3' (SEQ ID 3) |
| aroCpKD-R | Amplification of PCR product used for the allelic exchange of aroC | 5' TAT CAG TCT TCA CAT CGG CAT TTT GCG CCC GCT GCC GTA A*CA TAT GAA TAT CCT CCT TAG TTC CTA TTA A* 3' (SEQ ID 4) |
| rfbFpKD-F | Amplification of PCR product used for the allelic exchange of rfbF | 5' GAA TAG TAA TAT TTA CGC TGT CAT TGT GAC ATA TAA TCC CG*G TGT AGG CTG GAG CTG CTT C* 3' (SEQ ID 5) |
| rfbFpKD-R | Amplification of PCR product used for the allelic exchange of rfbF | 5' GCA TTA TAA CGA CCG CCC CCA GTA ATT CCT CTT ATT CC*C ATA TGA ATA TCC TCC TTA GTT CCT AAT CC* 3' (SEQ ID 6) |
| aro-ko1 | Confirmation of allelic exchange within aroC | 5' GAG CCG TGA TGG CTG GAA ACA C 3' (SEQ ID 7) |
| aro-ko2 | Confirmation of allelic exchange within aroC | 5' AGC GCA ATC GCG GTT TTG TTC A 3' (SEQ ID 8) |
| rfbF-ko1 | Confirmation of allelic exchange within rfbF | 5' GGG TTA CTG GGT GCC GCA ATA TCC 3' (SEQ ID 9) |
| rfbF-ko2 | Confirmation of allelic exchange within rfbF | 5' CCT CAA TCC AGC ATT CGC CAT TAT ACG 3' (SEQ ID 10) |

[a] The underlined sequence is specific to the helper plasmid used for the amplification of the antibiotic resistance cassette required for the mutagenesis

Fig. 7

>GP-P13F (SEQ ID 11)
GCTGCCGTGGTTCAAGTCGCGACTAATAAAAATAATCAGGTTGCCATGATTCAAT
GTACACCTTTCTCACATTCGTCTCCGGCATGAAAACGATGCACTCTTTCTTTATCG
CTTTCACTACACATTTTATCCTCGCATGGATGTTTTATAAAAAACATGATTGACATC
ATGTTGCATATAGGTTAAACAAAACAAGTGGCGTTATCTTTTCCGGATTGTCTTCT
TGTATGATATATAAGTTTTCCTCGATGAATAAAGTAAATGTTATGTTTTATTTACG
GCGTTACTATCCTCTCTATGTGCATACGGAGCTCCCCAGTCTATTACAGAACTATG
TTCGGAATATCGCAACACACAAATATATACGATAAATGACAAGATACTATCATATA
CGGAATCGATGGCAGGCAAAGAGAAATGGTTATCATTACATTTAAGAGCGGCGC
AACATTTCAGGTCGAAGTCCCGGGCAGTCAACATATAGACTCCCAAAAAAAGCC
ATTGAAAGGATGAAGGACACATTAAGAATCACATATCTGACCGAGACCAAAATTGA
TAAATTATGTGTATGGAATAATAAAACCCCCAATTCAATTGCGGCAATCAGTATGG
AAAACGGGCCGGGGCCCAATTCTTCTAACTACTGCTGTGAACTTTGTTGTAATTTT
GCCTGTACAGGATGTTACTAGTTTGCTTTAAAAGCATGTCTAATGCTAGGAACCTA
TATAACAACTACTGTACTTATACTAATGAGCCTTATGCTGCATTTGAAAAGGCGGT
AGAGGATGCAAT

>GP-P13F (SEQ ID 12)
MNKVKCYVLFTALLSSLCAYGAPQSITELCSEYRNTQIYTINDKILSYTESMAGKREMV
IITFKSGATFQVEVPGSQHIDSQKKAIERMKDTLRITYLTETKIDKLCVWNNKTPNSIAAI
SMENGPGPNSSNYCCELCCNFACTGCY

> GS-P13G (SEQ ID 13)
GCTGCCGTGGTTCAAGTCGCGACTAATAAAAATAATCAGGTTGCCATGATTCAAT
GTACACCTTTCTCACATTCGTCTCCGGCATGAAAACGATGCACTCTTTCTTTATCG
CTTTCACTACACATTTTATCCTCGCATGGATGTTTTATAAAAAACATGATTGACATC
ATGTTGCATATAGGTTAAACAAAACAAGTGGCGTTATCTTTTCCGGATTGTCTTCT
TGTATGATATATAAGTTTTCCTCGATGAATAAAGTAAATGTTATGTTTTATTTACG
GCGTTACTATCCTCTCTATGTGCATACGGAGCTCCCCAGTCTATTACAGAACTATG
TTCGGAATATCGCAACACACAAATATATACGATAAATGACAAGATACTATCATATA
CGGAATCGATGGCAGGCAAAGAGAAATGGTTATCATTACATTTAAGAGCGGCGC
AACATTTCAGGTCGAAGTCCCGGGCAGTCAACATATAGACTCCCAAAAAAAGCC
ATTGAAAGGATGAAGGACACATTAAGAATCACATATCTGACCGAGACCAAAATTGA
TAAATTATGTGTATGGAATAATAAAACCCCCAATTCAATTGCGGCAATCAGTATGG
AAAACGGCGGAGGTGGCTCCAATTCTTCTAACTACTGCTGTGAACTTTGTTGTAAT
GGCGCCTGTACAGGATGTTACTAGTTTGCTTTAAAAGCATGTCTAATGCTAGGAAC
CTATATAACAACTACTGTACTTATACTAATGAGCCTTATGCTGCATTTGAAAAGGC
GGTAGAGGATGCAAT

> GS-P13G (SEQ ID 14)
MNKVKCYVLFTALLSSLCAYGAPQSITELCSEYRNTQIYTINDKILSYTESMAGKREMV
IITFKSGATFQVEVPGSQHIDSQKKAIERMKDTLRITYLTETKIDKLCVWNNKTPNSIAAI
SMENGGGGSNSSNYCCELCCNGACTGCY

Fig. 7 (continued)

> GS-N12R (SEQ ID 15)
GCTGCCGTGGTTCAAGTCGCGACTAATAAAAATAATCAGGTTGCCATGATTCAAT
GTACACCTTTCTCACATTCGTCTCCGGCATGAAAACGATGCACTCTTTCTTTATCG
CTTTCACTACACATTTTATCCTCGCATGGATGTTTTATAAAAAACATGATTGACATC
ATGTTGCATATAGGTTAAACAAAACAAGTGGCGTTATCTTTTTCCGGATTGTCTTCT
TGTATGATATATAAGTTTTCCTCGATGAATAAAGTAAATGTTATGTTTTATTTACG
GCGTTACTATCCTCTCTATGTGCATACGGAGCTCCCCAGTCTATTACAGAACTATG
TTCGGAATATCGCAACACACAAATATATACGATAAATGACAAGATACTATCATATA
CGGAATCGATGGCAGGCAAAGAGAAATGGTTATCATTACATTTAAGAGCGGCGC
AACATTTCAGGTCGAAGTCCCGGGCAGTCAACATATAGACTCCCAAAAAAAGCC
ATTGAAAGGATGAAGGACACATTAAGAATCACATATCTGACCGAGACCAAAATTGA
TAAATTATGTGTATGGAATAATAAAACCCCAATTCAATTGCGGCAATCAGTATGG
AAAACGGCGGAGGTGGCTCCAATTCTTCTAACTACTGCTGTGAACTTTGTTGTCG
CCCTGCCTGTACAGGATGTTACTAGTTTGCTTTAAAAGCATGTCTAATGCTAGGAA
CCTATATAACAACTACTGTACTTATACTAATGAGCCTTATGCTGCATTTGAAAAGG
CGGTAGAGGATGCAAT

> GS-N12R (SEQ ID 16)
MNKVKCYVLFTALLSSLCAYGAPQSITELCSEYRNTQIYTINDKILSYTESMAGKREMV
IITFKSGATFQVEVPGSQHIDSQKKAIERMKDTLRITYLTETKIDKLCVWNNKTPNSIAAI
SMENGGGGSNSSNYCCELCCRPACTGCY

> GS-N12K (SEQ ID 17)
GCTGCCGTGGTTCAAGTCGCGACTAATAAAAATAATCAGGTTGCCATGATTCAAT
GTACACCTTTCTCACATTCGTCTCCGGCATGAAAACGATGCACTCTTTCTTTATCG
CTTTCACTACACATTTTATCCTCGCATGGATGTTTTATAAAAAACATGATTGACATC
ATGTTGCATATAGGTTAAACAAAACAAGTGGCGTTATCTTTTTCCGGATTGTCTTCT
TGTATGATATATAAGTTTTCCTCGATGAATAAAGTAAATGTTATGTTTTATTTACG
GCGTTACTATCCTCTCTATGTGCATACGGAGCTCCCCAGTCTATTACAGAACTATG
TTCGGAATATCGCAACACACAAATATATACGATAAATGACAAGATACTATCATATA
CGGAATCGATGGCAGGCAAAGAGAAATGGTTATCATTACATTTAAGAGCGGCGC
AACATTTCAGGTCGAAGTCCCGGGCAGTCAACATATAGACTCCCAAAAAAAGCC
ATTGAAAGGATGAAGGACACATTAAGAATCACATATCTGACCGAGACCAAAATTGA
TAAATTATGTGTATGGAATAATAAAACCCCAATTCAATTGCGGCAATCAGTATGG
AAAACGGCGGAGGTGGCTCCAATTCTTCTAACTACTGCTGTGAACTTTGTTGTAAA
CCTGCCTGTACAGGATGTTACTAGTTTGCTTTAAAAGCATGTCTAATGCTAGGAAC
CTATATAACAACTACTGTACTTATACTAATGAGCCTTATGCTGCATTTGAAAAGGC
GGTAGAGGATGCAAT

>-GS-N12K (SEQ ID 18)
MNKVKCYVLFTALLSSLCAYGAPQSITELCSEYRNTQIYTINDKILSYTESMAGKREMV
IITFKSGATFQVEVPGSQHIDSQKKAIERMKDTLRITYLTETKIDKLCVWNNKTPNSIAAI
SMENGGGGSNSSNYCCELCCKPACTGCY

Ipa co1 (SEQ ID 19)
GTAAGCACCACAACCACTGG

Fig. 7 (continued)

Ipa co2 (SEQ ID 20)
CCAGCAATCTGACTGGCTGTCG

Ipa pKD1 (SEQ ID 21)
GCCAAAATATTGGCTTCCACTGAGCTTGGAGACAATACTATCCAAGCCATATGAAT
ATCCTCCTTAGTTCCTAATCC

Ipa pKD2 (SEQ ID 22)
GTATTAATTGATTTGTCGCTTGGGATGCTTCTTTAGATACTTGGGGTGTAGGCTGG
AGCTGCTTC

IpaBC (SEQ ID 23)
ATGCATAATGTAAGCACCACAACCACTGGTTTTCCTCTTGCCAAAATATTGGCTTC
CACTGAGCTTGGAGACAATACTATCCAAGCTGCAAATGATGCAGCTAACAAATTAT
TTTCTCTTACAATTGCTGATCTTACTGCTAACCAAAATATTAATACAACTAATGCAC
ACTCAACTTCAAATATATTAATCCCTGAACTTAAAGCACCAAAGTCATTAAATGCAA
GTTCCCAACTAACGCTTTTAATTGGAAACCTTATTCAAATACTCGGTGAAAATCTT
TAACTGCATTAACAAATAAAATTACTGCTTGGAAGTCCCAGCAACAGGCAAGACA
GCAAAAAAACCTAGAATTCTCCGATAAAATTAACACTCTTCTATCTGAAACTGAAG
GACTAACCAGAGACTATGAAAACAAATTAATAAACTAAAAAACGCAGATTCTAAA
ATAAAAGACCTAGAAAATAAAATTAACCAAATTCAAACAAGATTATCCGAACTCGA
CCCAGAGTCACCAGAAAAGAAAAAATTAAGCCGGGAAGAAATACAACTCACTATC
AAAAAAGACGCAGCAGTTAAAGACAGGACATTGATTGAGCAGAAAACCCTGTCAA
TTCATAGCAAACTTACAGATAAATCAATGCAACTCGAAAAAGAAATAGACTCTTTTT
CTGCATTTTCAAACACAGCATCTGCTGAACAGCTATCAACCCAGCAGAAATCATTA
ACCGGACTTGCCAGTGTTACTCAATTGATGGCAACCTTTATTCAACTAGTTGGAAA
AAATAATGAAGAATCTTTAAAAAATGATCTGGCTCTATTCCAGTCTCTCCAAGAATC
AAGAAAAACTGAAATGGAGAGAAAATCTGATGAGTATGCTGCTGAAGTACGTAAA
GCAGAAGAACTCAACAGAGTAATGGGTTGTGTTGGGAAAATACTTGGGGCACTTT
TAACTATCGTTAGTGTTGTTGCAGCAGCTTTTTCTGGAGGAGCCTCTCTAGCACTG
GCAGCTGTTGGTTTAGCTCTTATGGTTACGGATGCTATAGTACAAGCAGCGACCG
GCAATTCCTTCATGGAACAAGCCCTGAATCCGATCATGAAAGCAGTCATTGAACC
CTTAATCAAACTCCTTTCAGATGCATTTACAAAAATGCTCGAAGGCTTGGGCGTCG
ACTCGAAAAAAGCCAAAATGATTGGCTCTATTCTGGGGGCAATCGCAGGCGCTCT
TGTCCTAGTTGCAGCAGTCGTTCTCGTAGCCACTGTTGGTAAACAGGCAGCAGCA
AAACTTGCAGAAAATATTGGCAAAATAATAGGTAAAACCCTCACAGACCTTATACC
AAAGTTTCTCAAGAATTTTTCTTCTCAACTGGACGATTTAATCACTAATGCTGTTGC
CAGATTAAATAAATTTCTTGGTGCAGCGGGTGATGAAGTAATATCCAAACAAATTA
TTTCCACCCATTTAAACCAAGCAGTTTTATTAGGAGAAAGTGTTAACTCTGCCACA
CAAGCGGGAGGAAGTGTCGCTTCTGCTGTTTTCCAGAACAGCGCGTCGACAAAT
CTAGCAGACCTGACATTATCGAAATATCAAGTTGAACAACTGTCAAAATATATCAG
TGAAGCAATAGAAAAATTCGGCCAATTGCAGGAAGTAATTGCAGATCTATTAGCCT
CAATGTCCAACTCTCAGGCTAATAGAACTGATGTTGCAAAAGCAATTTTGCAACAA
ACTACTGCTTGATACAAATAAGGAGAATGTTATGGAAATTCAAAACACAAAACCAA
CCCAGATTTTATATACAGATATATCCACAAAACAAACTCAAAGTTCTTCCGAAACAC
AAAAATCACAAAATTATCAGCAGATTGCAGCGCATATTCCACTTAATGTCGGTAAA
AATCCCGTATTAACAACCACATTAAATGATGATCAACTTTTAAAGTTATCAGAGCAG
GTTCAGCATGATTCAGAAATCATTGCTCGCCTTACTGACAAAAAGATGAAAGATCG

Fig. 7 (continued)

```
TTCAGAGATGAGTCACACCCTTACTCCAGAGAACACTCTGGATATTTCCAGTCTTT
CTTCTAATGCTGTTTCTTTAATTATTAGTGTAGCCGTTCTACTTTCTGCTCTCCGCA
CTGCAGAAACTAAATTGGGCTCTCAATTGTCATTGATTGCGTTCGATGCTACAAAA
TCAGCTGCAGAGAACATTGTTCGGCAAGGCCTGGCAGCCCTATCATCAAGCATTA
CTGGAGCAGTCACACAAGTAGGTATAACGGGTATCGGTGCCAAAAAAACGCATTC
AGGGATTAGCGACCAAAAAGGAGCCTTAAGAAAGAACCTTGCCACTGCTCAATCT
CTTGAAAAAGAGCTTGCAGGTTCTAAATTAGGGTTAAATAAACAAATAGATACAAA
TATCACCTCACCACAAACTAACTCTAGCACAAAATTTTTAGGTAAAAATAAACTGG
CGCCAGATAATATATCCCTGTCAACTGAACATAAAACTTCTCTTAGTTCTCCCGAT
ATTTCTTTGCAGGATAAAATTGACACCCAGAGAAGAACTTACGAGCTCAATACCCT
TTCTGCGCAGCAAAACAAAACATTGGCCGTGCAACAATGGAAACATCAGCCGTT
GCTGGTAATATATCCACATCAGGAGGGCGTTATGCATCTGCTCTTGAAGAAGAAG
AACAACTAATCAGTCAGGCCAGCAGTAAACAAGCAGAGGAAGCATCCCAAGTATC
TAAAGAAGCATCCCAAGCGACAAATCAATTAATACAAAAATTATTGAATATAATTGA
CAGCATCAACCAATCAAAGAATTCGACAGCCAGTCAGATTGCTGGTAACATTCGA
GCTTAA
```

PpA (SEQ ID: 24)

```
AAGTAAATAAAACGTTAATCACAAGTTTGTAATCGCTTTCATCTCACTATGAAAAAT
GCGGCTACGGTTATGGATTTTCCTGCTCTGTATACCGTCTTAAAACTGGCGAAAAA
GGAAAATGAAGACGAAAACAAGCAAAGACATTCGGCGCGAGTTGGCTATAATACT
TGGCACTTGTTTGCCACATATTTTTAAAGGAAACAGACATGAGCTTACTCAACGTC
CCTGCGGGTAAAGATCTGCCGGAAGACATCTACGTTGTTATTGAGATCCCGGCTA
ACGCAGATCCGATCAAATACGAAATCGACAAAGAGAGCGGCGCACTGTTCGTTGA
CCGCTTCATGTCCACCGCGATGTTCTATCCGTGCAACTACGGTTACATCAACCAC
ACCCTGTCTCTGGACGGTGACCCGGTTGACGTACTGGTCCCGACTCCGTACCCG
CTGCAGCCTGGTTCTGTGATCCGTTGCCGTCCGGTTGCCGTTCTGAAAATGACCG
ACGAAGCCGGTGAAGATGCAAAACTGGTTGCGGTTCCGCACAGCAAGCTGAGCA
AAGAATACGATACATTAAAGACGTAAACGATCTGCCTGAACTGCTGAAAGCGCA
AATCGCTCACTTCTTCGAGCACTACAAAGACCTCGAAAAAGGCAAGTGGGTGAAA
GTTGAAGGTTGGGAAAACGCAGAAGCCGCTAAAGCTGAAATCGTTGCTTCCTTCG
AGCGCGCAAAGAATAAATAAGTTCTTCTAGCGCAATAACCCTGAACGCCGGGCTT
CGGTTAGTAAGGGTTTTTTTATGCCCGCGATAAATAAACTCTCTATTCCACCATCA
TTATTCTCAGCGGTTGCAAGGCTTGAACGGTAAGAACAAGCAAACCCGACCACCA
TTTTGCTGTTCATAGCCACTTGCTGGAAGTTAGCCGACCTCACTCATACTCACCG
``` ppa pKD-F (SEQ ID: 25)
TTATTATTGGTGAAAAGATGTTCGCGAAAAAACTATAGACAATTCGTTATGTAACG
GATTGCGTTACATCGTGTAGGCTGGAGCTGCTTC ppa pKD-R (SEQ ID: 26)
TCCATATCTGCAATCGCATAAAAAACTCTGCTGGCGTTCACAAATGTGCAGGGGT
AAAACGGGGGCACGCCATATGAATATCCTCCTTAGTTCCTAATCC ppa ko1 (SEQ ID: 27)
CATAGGGTTGTCCTCGTCGGGG

Fig. 7 (continued)

ppa ko2 (SEQ ID: 28)
GTT TTA TGC GAT GTA TCT CGC G

Linker (SEQ ID 29)
GGGGS

LIVE ATTENUATED SHIGELLA VACCINE

The invention relates to a live attenuated *Shigella* vaccine strain generated with specific targeted mutations in order to induce serotype independent cross-protection and express heterologous (non-*Shigella*) antigens.

BACKGROUND

Shigellae are highly human-adopted Gram-negative enterobacteria causing bacillary dysentery. The disease spreads exclusively by direct personal contact or human fecal contamination of food and water. As a result, bacillary dysentery is endemic in regions with suboptimal hygienic conditions. There are an estimated 165M cases worldwide, with as many as 1M fatalities mostly among children under the age of five *Shigella* was found to be the one of the most prevalent bacterial pathogen isolated in case of an acute diarrheal episode among 1-5 year-old children in Southeast Asia and sub-Saharan Africa (Kotloff et al., Bull. W.H.O. 77: 651-666, 1999). Bacillary dysentery is also common among travelers and military personnel entering endemic countries. It has long been accepted that vaccines would be crucial to control dysentery but vaccine development against Shigellae is hampered by the serotype-specific immune response, i.e upon exposure to *Shigella* (natural or vaccine-mediated) the immune protection is usually limited to the given serotype. The four species of the *Shigella* genus comprise a sum of 50 serotypes and subserotypes, which are differentiated by their LPS O-antigens.

Hong et al. (Molecular Microbiology 24:779-91, 1997) described the effect of mutations in chromosomal and plasmid-encoded lipopolysaccharide genes on invasion and serum resistance of *Shigella flexneri*. Mutations in the rfb and rfaL genes either eliminated the entire O-antigen side chains or produced chains of greatly reduced length.

Nagy et al. (J. Infect. Diseases 198: 1699-706, 2008) described the vaccine potential of a *Salmonella enterica* regulatory lipopolysaccharide mutant. Loss of the transcriptional antiterminator RfaH resulted in a heterogeneous length of LPS chains, the "gently rough" phenotype.

Regulatory protein RfaH is shown to be involved in the growth-phase dependent upregulation of long-chained (i.e. high number of O-antigen repeat) LPS molecules of *S. flexneri* (Carter et al. Microbiology. 2007 October; 153 (Pt 10):3499-507).

Major virulence factors of Shigellae other than LPS O-antigens are surprisingly conserved. This implies a lack of immune-mediated evolutionary pressure on these antigens substantiating the accepted view about O-antigen being the sole protective antigen. Nevertheless, there is a marked antibody response against the so-called "invasion plasmid antigens" (Ipa-s), especially following repeated exposure. These antigens encoded on the large virulence plasmid form components of a type three secretion system (T3SS) that is indispensable for invasion and hence virulence.

The structure-function analysis of the *Shigella* virulence factor invasion plasmid antigen B (ipaB) was disclosed by Guichon et al. (J. Bacteriol. 183:1269-76, 2001). ipaB mutants were generated to correlate function with protein subdomains.

Menard et al. (J. Bacteriol. 17518: 5899-5906, 1993) described that mutagenesis of the ipa genes ipaB, ipaC and ipaD of *Shigella flexneri*, resulted in the loss of invasive potential of *Shigella*.

Antibodies against Ipa proteins (such as to minor conserved antigens) are considered non-protective, as otherwise cross-protection among serotypes could be triggered. Current vaccine approaches rely almost exclusively on O-antigen mediated immunity exploiting the fact that five or six serotypes would provide high protection against the majority of endemic and epidemic dysentery cases. Nevertheless, considering the fact that most of the suggested multivalent vaccines are based on either purified subunits (O-antigens) or several live attenuated bacteria with different LPS O-antigen types, they would, most probably, be too complex and hence expensive. Moreover, a partial serotype coverage is expected to induce serotype replacement due to herd immunity based immune pressure on vaccine serotypes and escape and increase in prevalence of non-vaccine serotypes, as demonstrated for other multi-serotype pathogens, such as *Streptococcus pneumoniae*. Therefore, an ideal *Shigella* vaccine is expected to provide substantial cross-protection against all circulating serotypes.

Besides *Shigella*, Enterotoxigenic *Escherichia coli* (ETEC) is a major bacterial pathogen responsible for travelers' diarrhea and represent one of the leading cause of death in children in endemic countries. Therefore efforts are undertaken to develop vaccines addressing these two pathogens simultaneously.

Travelers' diarrhea is currently treated by antibiotics; however, there is an increasing rate of resistance among *Shigella* strains that makes the management of the disease more and more difficult. Moreover, ETEC infections can have long-term consequences related to irritable colon syndrome. It is widely accepted that vaccination would be the most effective way to address this high unmet medical need; yet, no vaccines are currently available for the prevention of these conditions.

Two types of enterotoxins have been identified in ETEC strains, the heat labile toxin (LT) and the heat stable toxin (ST), either as ST associated with porcine disease (STp) or ST associated with human disease (STa). LT is highly homologous in structure to the cholera toxin. The A subunit is the active component of the toxin, which functions to increase the activity of adenylate cyclase. This is delivered into host cells by the B subunits, which bind to gangliosides on the cell surface. STa is a small (19 amino acid) non-immunogenic polypeptide that has guanylate cyclase stimulating activity. STm is a mutated form of ST that is non-toxic, but still immunogenic. Such STm is considered to be safely employed as vaccine antigen (Taxt et al. Infect. Immun. 78:1824-31, 2010).

It has been demonstrated that ETEC strains also produce EAST1, a heat-stable toxin similar in size and mode of action to ST but different in sequence, originally identified in enteroaggregative *E. coli* strains (Nataro and Kaper, Clin Microbial Rev. 11: 142-201, 1998; Zhang et al., Vet Microbial. 123: 145-152, 2007).

Zheng et al. (World J. Gastroeneterol. 11: 3411-18, 2005) constructed an asd mutant *Shigella* strain co-expressing CS3 and LTB/STm of enterotoxigenic *E. coli*. After immunization of mice by the oral route, antibodies were raised against CS3, LTB, ST, and *Shigella* lipopolysaccharide.

Xu et al. (Vaccine 21: 664-648, 2003) described a live attenuated invasive *Shigella flexneri* serotype 2a rfbF mutant as a carrier for a DNA-based HIV gag vaccine.

Noriega et al. (Infection and Immunity 67(2): 782-788, 1999) described a strategy for cross-protection against 14 *Shigella flexneri* serotypes, involving the use of the two serotypes 2a and 3a. The attenuated strains described are *S. flexneri* 2a strain CVD1207 (ΔguaB-A Δset1 Δsen) and *S. flexneri* 3a strain CVD 1211 (ΔguaB-A ΔvirG Δsen).

Bernardini et al. (Infection and Immunity 69(2): 1072-1083, 2001) describe mutants of *Shigella flexneri* 5, which are an aroC mutant and a double purE aroC mutant.

Levine et al. (Behring Institute Mitteilungen 98: 120-123, 1997) described an attenuated *S. flexneri* 2a strain CVD 1203 which harbors mutations in chromosomal gene aroA and plasmid gene virG, as well as an *S. flexneri* 2a vaccine candidate CVD 1205 that harbors a deletion mutation in guaB-A rendering it defective in nucleic acid synthesis, and a deletion mutation in virG.

It is the objective of the present invention to provide improved *Shigella* vaccines, in particular for the prevention of diarrheal diseases that are highly relevant for travelers to endemic countries and young children living in developing countries. Such vaccines can be based on a live attenuated *Shigella flexneri* vaccine strain able to heterogeneously express antigens derived from different pathogens and induce broad protection against bacterial pathogens, and particularly shigellosis.

SUMMARY OF THE INVENTION

The object is solved by the subject matter as claimed.

According to the invention there is provided a live attenuated *Shigella* vaccine, which is based on a rough *Shigella* strain lacking LPS 0 antigen.

Specifically, the *Shigella* strain is non-invasive by mutagenesis, in particular a mutation of the invasion plasmid.

Specifically the vaccine according to the invention is attenuated by mutagenesis of one or more genes involved in the LPS synthesis, transport and expression, preferably selected from the group consisting of genes in the cluster of the rib operon, e.g. located on the chromosome between Gnd (6-phosphogluconate dehydrogenase, 2089155-2090561) and GalF (UTP-glucose-1-phosphate uridyltransferase, 2101928-2102821) genes of the *Shigella flexneri* 2a 2457T strain (Wei et al. Complete genome sequence and comparative genomics of *Shigella flexneri* serotype 2a strain 2457T. Infect Immun. 2003 May; 71(5):2775-86.) or located on the virulence plasmid (*Shigella sonnei*). Specifically preferred is the mutagenesis of one or more genes within the rfb/wbb gene cluster encoding O-antigen synthesis, waaL encoding the O-antigen ligase, wzx encoding O-antigen flippase involved in O-antigen transport, wzy/rfc involved in O-antigen polymerization, genes within the rfa/waa gene cluster encoding LPS-core synthesis, regulatory genes affecting O-antigen expression, such as rfaH, or loss of function(s) of which results in at least 90% reduction in the expression of O-antigens.

According to a specific embodiment, said mutagenesis is by a deletion of one or more of the rfb F, D, C, E, J and/or I genes, or a deletion of a part thereof, or corresponding genes in various *Shigella* serotypes. Alternatively, mutagenesis by inactivation, e.g. transient, conditional or constitutive inactivation, may be employed.

Said *Shigella* strain is preferably selected from the genus *Shigella*, e.g. from any *Shigella* serotypes or species, in particular *S. flexneri, S. sonnei, S. dysenteriae* and *S. boydii*.

Specifically, said *Shigella* strain expresses outer membrane proteins, which can induce cross-reactive antibodies, in particular conserved proteins, including OmpC, OmpA and OmpX, or those encoded on the invasion plasmid.

The vaccine according to the invention is particularly cross-protective against different serotypes and species of *Shigella*, in particular against any of *S. flexneri* 2a, *S. flexneri* 6 and *S. sonnei*, or enteroinvasive *Escherichia coli*.

According to a specific aspect, said *Shigella* is non-invasive by further mutagenesis of the invasion plasmid, in particular a mutation of the invasion plasmid, which comprises a deletion of the ipaB and/or ipaC and/or other ipa genes.

Specifically, said *Shigella* comprises a recombinant endogenous invasion plasmid incorporating at least one gene encoding a heterologous antigen to secrete said antigen or to express said antigen on the bacterial cell surface.

Preferred embodiments refer to such vaccine, wherein said antigen is a protective antigen derived from a pathogen, e.g. selected from the group consisting of
- a bacterial antigen preferably a toxin or colonization factor,
- a viral antigen, preferably from a pathogen causing enteral or mucosal infections,
- a fungal antigen, preferably from a pathogen causing enteral or mucosal infections, and
- a parasitic antigen, preferably from a pathogen causing enteral infections.

Specifically, the bacterial antigen is originating from enteropathogenic bacteria, preferably selected from the group consisting of
a. *E. coli* antigens, in particular an enterotoxin selected from the group consisting of LTB, mutated LTA and ST of ETEC, subunits, or fusions thereof, antigens from enteroaggregative *E. coli* (EAEC), or Shiga-like toxin 1 or 2
b. *Campylobacter jejuni* antigens,
c. *Clostridium difficile* antigens, specifically toxins A and B
d. *Vibrio cholera* antigens, specifically the CT-B antigen, and
e. mutants or fusion proteins of a), b) c) or d).

Specifically, the bacterial antigen is an enterotoxin (ETEC) comprising the B subunit of heat labile toxin (LTB), the heat stable toxin (ST) or subunits or fusions thereof, preferably LTB/STm comprising an STm with an amino acid sequence as shown in SEQ ID 1, which optionally excludes the wild-type sequence of human ST.

In particular, said ETEC antigen is a fusion protein of the B subunit of LT and mutant ST, preferably a fusion protein LTB/STm with an amino acid sequence as derived from FIG. 7 SEQ ID 11-18 (LTA-promoter-LTB-ST-LTB terminator nucleotide and LTB-ST amino acid sequences for 4 constructs), for example with ST mutations at position 13 and/or 12, such as P13F or P13G, and/or N12R or N12K).

Specifically, the viral antigen is originating from diarrheal viruses, preferably selected from the group consisting of rotaviruses and Norwalk virus (caliciviruses).

Specifically, the parasite antigen is originating from diarrhea-causing protozoa, preferably selected from the group consisting of *Giardia lamblia, Cryptosporidium* species and *Entameba histolytica*.

Specifically, the fungal antigen is originating from diarrhea-causing fungi, preferably selected from the group consisting of *Blastomyces dermatiditis* and *Histoplasma* spp.

According to a specific aspect of the invention, the *Shigella* vaccine strain further comprises a deletion of an essential chromosomal gene and an insertion of said gene into the invasion plasmid, in particular the ppa gene, or any of accD, acpS, dapE, era, frr, ftsI, ftsL, ftsN, ftsZ, infA, lgt, lpxC, msbA, murA, murI, nadE, parC, proS, pyrB, rpsB, trmA, rho and rhoL.

Yet, according to a specific embodiment of the invention, the vaccine is provided for use in the prophylaxis or immunoprophylaxis of a subject to prevent infectious diseases, in particular enteral disease, such as diarrheal disease. Specifically, the disease is selected from the group consisting of Shigellosis, dysentery and diarrhea.

According to the invention, there is further provided a method of preventing infectious disease in a subject, in particular enteral disease, specifically by vaccination and immunizing said subject, respectively.

Specifically, said enteral disease is caused by any *Shigella* serotype or species.

Preferably, said (immune) prophylaxis comprises administration of the vaccine in a mucosal or oral formulation.

Specifically, the vaccine is administered orally or intranasally.

A specific embodiment refers to a vaccine for use according to the invention, wherein
- a polyvalent vaccine is used expressing protective antigens of *Shigella* and at least one other one of a species other than *Shigella* by the incorporation of a protective antigen of said pathogen into the endogenous modified recombinant invasion plasmid, and wherein
- said infectious disease is caused by any *Shigella* serotype or species and/or said pathogen.

According to a further aspect of the invention, there is provided a *Shigella* strain, which is a *S. flexneri* 2a strain, such as *S. flexneri* 2a 2457T, with a deletion of the rfbF and at least one of the ipaB and/or ipaC genes, or a deletion of essential parts thereof.

Specifically, said *Shigella* strain may further comprise a deletion of an essential chromosomal gene and an insertion of said gene into the invasion plasmid.

Preferably, said *Shigella* strain comprises a recombinant invasion plasmid incorporating at least one gene encoding a heterologous antigen to express and/or secrete said antigen.

Yet, according to a further aspect of the invention, there is provided a recombinant plasmid vector based on a mutated *Shigella* invasion plasmid comprising a nucleotide sequence encoding at least one heterologous antigen, wherein the plasmid is mutated in at least one of the ipaB and/or ipaC genes. This specifically refers to a mutation for the deletion and/or inactivation of a non-coding or coding region, such as regulatory sequences operably linked to a gene and a gene, respectively, preferably a deletion of the genes that renders the bacterial host cell non-invasive, in particular a deletion of the ipaB and/or ipaC genes, or a deletion of a (substantial) part thereof.

A further specific aspect of the invention relates to a bacterial host cell comprising the vector according to the invention, wherein said host cell is specifically selected from the genera *Shigella*, *Escherichia*, *Salmonella*, *Campylobacter* or *Yersinia*.

Said host cell specifically comprises a mutation in the endogenous invasion plasmid. Specifically, the vector according to the invention is an endogenous invasion plasmid, i.e. a plasmid endogenous or homologous to the host cell.

FIGURES

FIG. 1. Cross-Protective Capacity of Live Attenuated Non-Invasive Strains of *S. flexneri* and *S. sonnei* Lacking LPS O-Antigen Synthesis.

Groups of 8 week-old BALB/c mice were immunized intranasally with CRP ($10^6$ CFU) and CRN ($10^8$ CFU) variants of *S. flexneri* 2a (a and b) mutants or alternatively phase I ($10^{5.5}$ CFU) and phase II ($10^{7.5}$ CFU) variants of *S. sonnei* (c) twice with two week-intervals. Control groups were mock vaccinated with saline. Subsequently, mice were challenged with either $10^6$ CFU of wild-type *S. flexneri* 6 (a and c) or $10^{6.5}$ CFU of wild-type *S. sonnei* (b) via the same route. Survival was monitored subsequently for 14 days. Figures show combined data of three (b) or two (a and c) independent experiments with 5 mice in each group and repeat. Statistical analysis of the survival curves was performed by the Log-rank (Mantel-Cox) test. In case survival was significantly different from that of mock-vaccinated mice, the p value is shown on the graph.

FIG. 2. Schematic Representation of Antigenic Phenotypes of the Various Mutants Used as Well as the Proposed Difference in Antibody Levels they Might Induce.

O-antigens, its genetic determinants, and the antibodies triggered by them are shown. Ipa and minor conserved surface antigens are shown. Mutants expressing both Ipa and O-antigens (*S. flexneri* ΔaroC CRP and *S. sonnei* Phase I) trigger an antibody response mainly against these major antigens. In contrast, loss of these antigens in the vaccine strains allows a higher response to minor conserved antigens. ip: invasion plasmid, chr.: chromosome, T3SS: type tree secretion system, LPS: lipopolysaccharide.

FIG. 3. Broad-reactive mucosal IgA obtained from mice vaccinated with live attenuated *S. flexneri* 2a strains. Immune reactivity of sIgA in BAL samples collected after 2 immunizations with the smooth ipa-positive strain (ΔaroC CRP) and the double mutant (ΔrfbF CRN) were determined in ELISA on different target bacterial cells. Reactivity is expressed as ratio (reactivity of the ΔaroC CRP sample divided by reactivity of the ΔrfbF CRN sample) at the same dilution in order to make repetitions comparable. Graph shows means+standard error of the means of four experiments performed with BAL samples obtained from independent vaccinations. Data were statistically compared by the Mann-Whitney non parametric test to the value obtained on the double (ipa and O antigen) positive target (ΔaroC CRP; black column).

FIG. 4. Supplementary Table 1: Oligonucleotides Used for the Generation and Confirmation of Deletion Mutants. (SEQ ID 3-10)

Figures 5A, 5B, 5C:
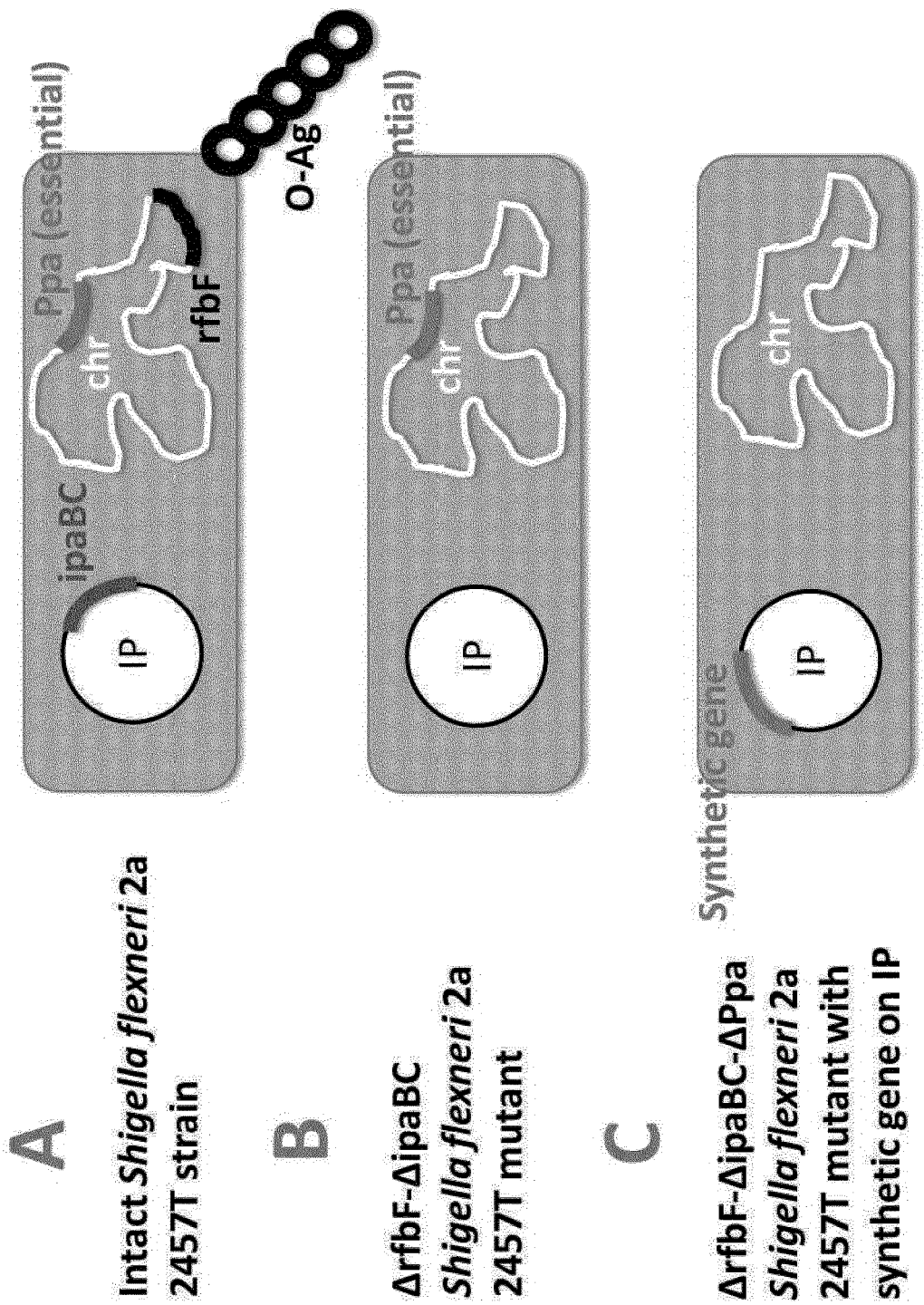

FIG. 5. Schematic Presentation of an Attenuated *Shigella flexneri* 2a 2457T Strain.
- A. The *Shigella flexneri* 2a 2457T fully sequenced strain. O-antigen is the serotype determinant of Shigellae. The rfbF gene on the *Shigella* chromosome encodes a factor essential for the synthesis of the O-antigen component of LPS. The invasion plasmid present in all pathogenic *Shigella* strains encodes the invasion plasmid antigens (IpaA-D) which are important molecular components of the type III secretion system (T3SS). T3SS mediates key processes of target cell-*Shigella* interactions and eventually leads to the transmission of *Shigella* factors into the target cell that enables the pathogen to invade and spread. Ipa B and IpaC are key and essential components of this system.
- B. In the *Shigella flexneri* 2a T2457 rfbF⁻ipaB/C⁻ mutant two deletions are introduced. Deletion of the rfbF gene from the chromosome eliminates the synthesis of the O-antigen and results in a "rough" strain that is attenuated and induces serotype independent immunity upon vaccination. Deletion of the ipaB and C genes on the invasion plasmid disrupts T3SS, thus rendering the *Shigella* mutant non-invasive (and Congo Red negative).
- C. In order to stabilize the invasion plasmid of the mutant *Shigella* strain, an essential chromosomal gene (inorganic pyrophosphatase, ppa (FIG. 7 SEQ ID 24)) is deleted from the chromosome and re-introduced as a part of the synthetic construct into the invasion plasmid.

Figure 6:
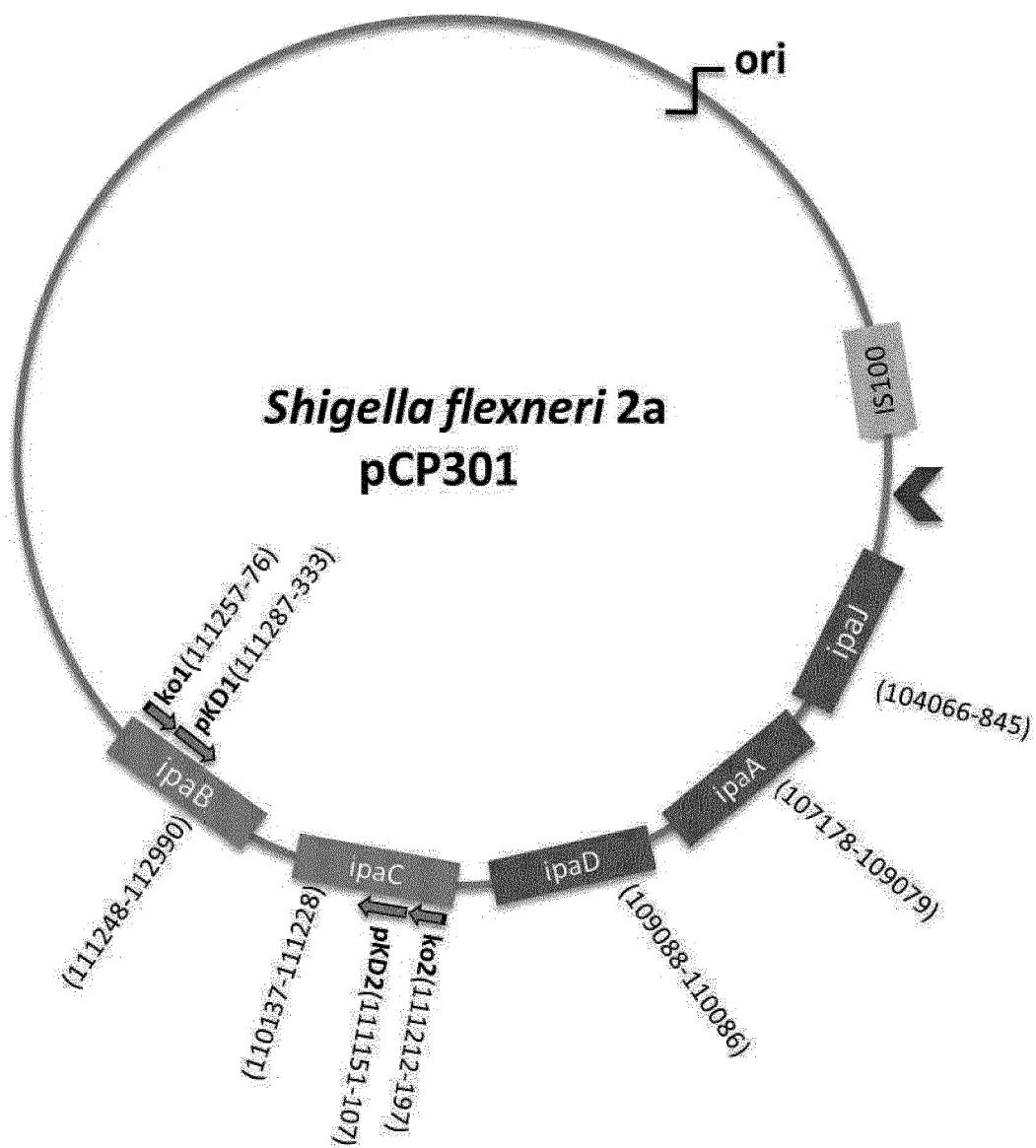

FIG. 6: Schematic illustration of the invasion plasmid pCP301 of the *Shigella flexneri* 2a 301 strain with the ipa cluster, the primer positions for ipaB/C deletion (pKD1,2) and the control primers for monitoring deletion of ipaB/C (ko1,2). Position of the insertion site of the synthetic gene between ipaJ and an IS100 element is also indicated.

FIG. 7: Sequences
gene for LT-B/mST fusion protein encoding ST with a mutation at amino acid position 13 (from Pro to Phe) together with the eltAB promoter and termination sequences
 GP-P13F (nucleotide sequence, SEQ ID 11),
LT-B/mST fusion protein with a mutation in ST at amino acid position 13 (from Pro to Phe)
 GP-P13F (amino acid sequence, SEQ ID 12), gene for LT-B/mST fusion protein encoding ST with a mutation at amino acid position 13 (from Pro to Gly) together with the eltAB promoter and termination sequences
 GS-P13G (nucleotide sequence, SEQ ID 13),
LT-B/mST fusion protein with a mutation in ST at amino acid position 13 (from Pro to Gly)
 GS-P13G (amino acid sequence, SEQ ID 14),
gene for LT-B/mST fusion protein encoding ST with a mutation at amino acid position 12 (from Asn to Arg) together with the eltAB promoter and termination sequences
 GS-N12R (nucleotide sequence, SEQ ID 15),
LT-B/mST fusion protein with a mutation in ST at amino acid position 12 (from Asn to Arg)
 GS-N12R (amino acid sequence, SEQ ID 16),
gene for LT-B/mST fusion protein encoding ST with a mutation at amino acid position 12 (from Asn to Lys) together with the eltAB promoter and termination sequences
 GS-N12K (nucleotide sequence, SEQ ID 17),
LT-B/mST fusion protein with a mutation in ST at amino acid position 12 (from Asn to Lys)
 GS-N12K (amino acid sequence, SEQ ID 18),
Forward control PCR primer for confirming ipa deletion mutant strains
 ipa co1 (SEQ ID 19),
Reverse control PCR primer for confirming ipa deletion mutant strains ipa co2 (SEQ ID 20),
Forward PCR primer to generate ipa deletion mutant strains
 ipa pKD1 (SEQ ID 21),
Forward PCR primer to generate ipa deletion mutant strains
 ipa pKD2 (SEQ ID 22),
Nucleotide sequence of the ipaB and ipC genes removed from the invasion plasmid
 ipaBC (SEQ ID 23).
Nucleotide sequence of the ppa gene implanted from the chromosome to the invasion plasmid
 *Shigella* ppa gene (SEQ ID 24).
Forward PCR primer to generate ppa deletion mutant strains
 ppa pKD-F (SEQ ID 25)
Reverse PCR primer to generate ppa deletion mutant strains
 ppa pKD-R (SEQ ID 26)
Forward control PCR primer for confirming ppa deletion mutant strains
 ppa ko1 (SEQ ID 27)
Reverse control PCR primer for confirming ppa deletion mutant strains
 ppa ko2 (SEQ ID 28)
Linker peptide inserted between LT-B and mST for flexible folding
 GGGGS (SEQ ID 29)

Figure 8:
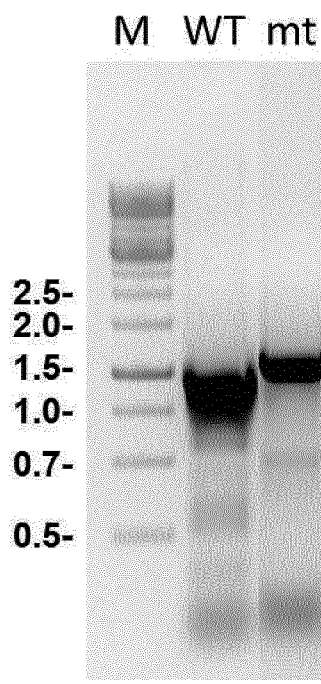

FIG. 8:
PCR amplification of the chromosomal region where the rfbF gene is deleted. M: DNA size marker; WT: wild type *Shigella flexneri* 2a 2457T, rfbF gene with flanking region, 1100 bp fragment; mt: ΔrfbF mutant, gene replacement with chloramphenicol gene, 1300 bp.

Figure 9:
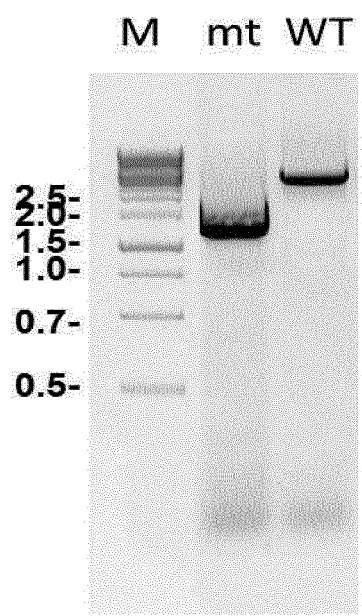

FIG. 9:
PCR amplification of the invasion plasmid region where the ipaC and ipaB genes were deleted. M: DNA size marker; WT: wild type *Shigella flexneri* 2a 2457T, ipaB and ipaC genes with flanking region, 1600 bp fragment; mt: ΔipaBC mutant invasion plasmid, gene replacement with kanamycin gene, 2570 bp.

Figure 10A:
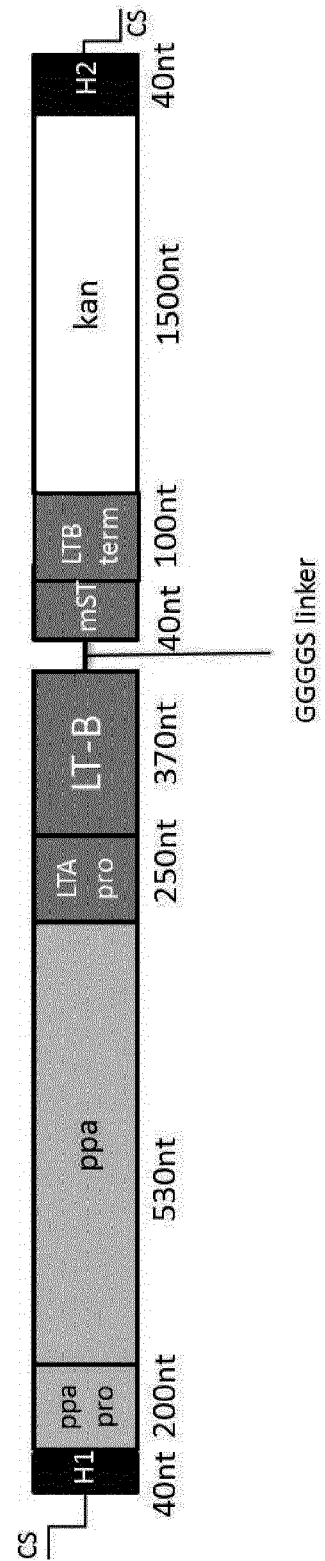

FIG. 10:
A. Structure of the multi-gene constructs encoding the essential gene Ppa, the LTB-mST fusion protein and the kanamycin resistance protein. Expression of the LTB-mST fusion protein is driven by the LTA-promoter and transcription is terminated with the LTB terminator. The LTB-ST amino acid sequences of 4 constructs with detoxifying ST mutations (P13F, P13G, N12R, N12K) are indicated (mutated codons underlined). Abbreviations: CS: cloning site; H1 and H2: homologous regions 1 and 2 on the invasion plasmid to aid homologous recombination; ppa: inorganic pyrophosphatase gene; pro: promoter; term: terminator; GGGGS: Gly-Gly-Gly-Gly-Ser (SEQ ID 29 penta-amino acid linker between LTB and mST; kan: kanamycin resistance gene.
B. Insertion of ETEC genes into the *Shigella* invasion plasmid. M: DNA size marker; WT: wild type *Shigella flexneri* 2a 2457T, invasion plasmid intergenic region, 450 bp fragment; mt: LT-B+STm gene mutant invasion plasmid, gene replacement with the kanamycin gene, 2800 bp,
C. Immunoblot analysis to detect LTB. The recombinant LT-B, as well *E. coli* and *Shigella* culture supernatant fractions (secreted proteins) were separated by SDS-PAGE, proteins transferred to nitrocellulose membrane and detected with the anti-LTB monoclonal antibody. Lane 1: wild type *Shigella flexneri* (negative control); lane 2: *Shigella flexneri* carrying the fusion gene in the invasion plasmid; lane 3: DH5α *E. coli* transformed with pGET vector containing the synthetic construct as shown in FIG. 10A lane 4: ETEC strain expressing LT (positive control).

Figure 11:
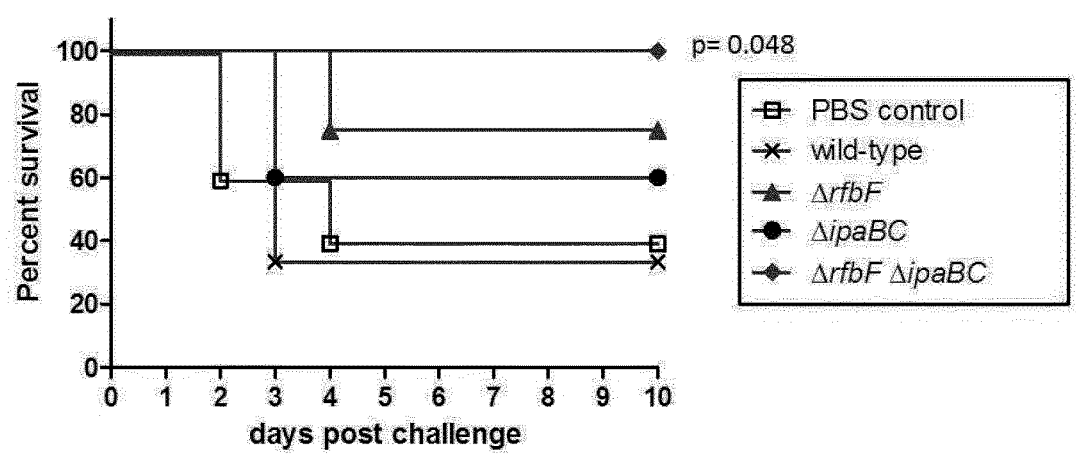

FIG. 11:
Heterologous protection induced by *Shigella flexneri* 2a vaccine strain with engineered rfbF and ipaC/ipaB combined mutation. Groups of 5 mice were immunized intranasally with sublethal doses of either wild-type strain *Shigella flexneri* 2a 2457T ($5 \times 10^5$ cfu/mouse) or its isogenic deletion mutants 2457TΔrfb, 2457TΔipaBC, 2457TΔrfbΔipaBC (all at $10^8$ cfu/mouse), or mock immunized with PBS buffer. Three identical immunizations were performed with 2-week intervals. One week following the last booster immunization, mice were challenged with a lethal dose of a *S. sonnei* strain ($2 \times 10^6$ cfu/mouse). Survival of animals was monitored daily.

DETAILED DESCRIPTION OF THE INVENTION

Specific terms as used throughout the specification have the following meaning.
The term "attenuated" is used herein to describe a virulent strain of *Shigella* that has been modified so that it is no longer capable of causing disease, i.e., the modified strain is avirulent. The term "live" regarding the attenuated *Shigella* is used herein to describe *Shigella* that is able to grow and reproduce. Accordingly, the live *Shigella* strain of the present invention is used in the attenuated live vaccine and is specifically able to colonise the colon of a subject, but not cause the clinical symptoms associated with enteral diseases caused by the enteral or diarrheal pathogens. Further, the live strain of the present invention is specifically capable of limited replication in the vaccinated subject and of inducing a protective immune response which is protective against virulent strains of *Shigella*. An attenuated bacterium of the invention may be genetically engineered to express a heterologous antigen that is not expressed by the native bacterium, so that the attenuated bacterium acts as a carrier of the heterologous antigen.

The term "antigen" as used according to the present invention shall in particular refer to any antigenic determinant, which can be possibly recognised by a binding site of an antibody. Specifically preferred antigens are those molecules or structures, which have already been proven to be or are capable of being immunologically or therapeutically relevant, especially those, for which a clinical efficacy has been tested. The term as used herein shall in particular comprise molecules or structures selected from antigens comprising immunoaccessible and immunorelevant epitopes, in particular conserved antigens found in one or more species or serotype. Immunoaccessible epitopes are typically presented by or comprised in antigens expressed on a cell surface. The term "protective antigen" as used herein shall refer to those antigens that trigger an immune response in vivo, so to induce neutralizing antibodies against the antigen. This provides for the effective protection upon active immunization with the antigen. Protein antigens are preferred antigens due to their inherent ability to elicit both cellular and humoral immune responses.

The term "heterologous" is herein used specifically with regard to an antigen, and understood as an antigen foreign to the cell expressing said heterologous antigen. With regard to a *Shigella* cell or strain, the term specifically refers to antigens foreign to the *Shigella* cell or strain, respectively. Thus, such heterologous or foreign antigen would not be expressed in a wild-type cell or strain, but by the recombinant one comprising a heterologous gene encoding said antigen. Thereby said recombinant cell or strain would express said heterologous antigen, e.g. on the cell surface. The cells of the invention may be genetically engineered to express a heterologous antigen, e.g. a non-toxic component or form of LT and/or ST or STm. Such cells induce an immune response against the heterologous antigen as well as the native antigens and hence improve the protection provided by a vaccine.

The term "cross-reactive" with respect to antigens as used herein shall mean antigens with epitopes shared between different pathogens, including e.g. different serotypes of the same species or different bacterial species. Cross-reactive antigens typically are conserved structures. Cross-reactive epitopes may originate from the same antigens expressed by different pathogens, or else from different antigens with similar structure.

Specific cross-reactive antigens are recognized by cross-reactive antibodies, e.g. antibodies of antisera, isolated antibodies or recombinant ones. Such cross-reactive antibodies may recognize the cross-reactive antigens of different pathogens. Specific cross-reactive antibodies are neutralizing antibodies.

A "cross-protective" vaccine or immune response is understood as one which protects against infection by at least one different pathogen, e.g. a different species or serotype, which is not identical to the one used to elicit the response. Cross-protective efficacy typically may be tested with different antisera from subjects that had been exposed to the different pathogens.

When a cross-reactive antigen is designed to induce cross-protective immunity, this may be tested in animal models, e.g. by immunising the animals with the cross-reactive antigen derived from one pathogen triggering an immune response, and challenging the animals with at least one pathogen different form the one used to elicit the response. As an example, such cross-protective immunity against more than one *Shigella* serotype or other enteroinvasive bacteria with cross-reactive antigens, such as *E. coli*, specifically refers to protection against distinct variations within the species of bacteria of different individuals, e.g. variations at the sub-species level. The group of serovars with common antigens is called a serogroup or serotype.

The basis for the development of a broad spectrum, e.g. multi-strain and/or multi-serotype and/or multi-species *Shigella* vaccine is the identification of cross-reactive antigens which are prevalent in *Shigella* serovars. This particularly includes isolates associated with human infections.

When a polyvalent vaccine is designed to induce cross-protective immunity against different pathogens, the immune response typically is elicited by several antigens, e.g. individual antigens from the different pathogens. As an example, such polyvalent vaccine may be based on at least two different protective antigens from different species, such as derived from *Shigella* and *Escherichia*, but also other bacterial, viral, fungal or parasitic antigens. The cross-protective, polyvalent vaccine may e.g. be tested in an animal model by immunising the animals with the vaccine comprising different protective antigens derived from at least two different pathogens triggering an immune response, and challenging the animals with one, two or more of the pathogens.

The basis for the development of a multi-species vaccine candidate based on specific attenuated *Shigella* bacteria, as used according to the invention, is the identification of protective antigens, either cross-reactive to address a series of different serotypes or not, which are prevalent in the different pathogenic species, against which protection is sought.

The term "enteral" also known as "enteric", as used herein specifically in connection with a disease or pathogen shall refer to a disease condition or pathogen relating to, or affecting the intestines, e.g. dysentery or diarrheal disease. Specifically such enteral disease refers to infectious disease of the colon. Specific symptoms include bloody, mucus-filled diarrhea; abdominal pain; fever and loss of fluids from the body. Diarrheal disease refers to conditions resulting in three or more loose or liquid stools per day, or as having more stools than is normal for that person. An enteral pathogen is understood to cause enteral disease in a subject, either upon infection with said pathogen, or intoxication of the subject with a toxin, in particular an enterotoxin.

There are many causes of infectious enteral disease, such as dysentery or diarrhea, which include viruses, bacteria, funghi and parasites. Examples are provided as follows: Norovirus is the most common cause of viral diarrhea in adults, but rotavirus is the most common cause in children under five years old. Adenovirus types 40 and 41, and astroviruses cause a significant number of infections. The bacterium *Campylobacter* is a common cause of bacterial dysentery or diarrhea, but infections by Salmonellae, Shigellae and some strains of *Escherichia coli* (*E. coli*) are frequent in some territories. In the elderly, particularly those who have been treated with antibiotics for unrelated infections, a toxin produced by *Clostridium difficile* often causes severe diarrhea. Examples of parasites include *Giardia lamblia*, which can cause chronic infections, and *Entamoeba histolytica*. Exemplary enteral disease as possibly addressed by the vaccine of the invention is Shigellosis and ETEC-related diarrhea.

The term "endogenous" as used herein with respect to a plasmid shall mean the plasmid that originates in a particular host cell. An endogenous plasmid may be genetically engineered to obtain a recombinant endogenous plasmid, e.g. by recombinant techniques to engineer the plasmid in situ, i.e. within the host cell harbouring the native endogenous plasmid, or else upon removal from the host cell, subjecting it to laboratory manipulation, and then reintroduced into a host cell of the same type. The invasive phenotype of *Shigella* is specifically conferred by the endogenous 220-kb virulence plasmid, also called invasion plasmid, or native or endogenous invasion plasmid. The endogenous invasion plasmid of *Shigella* is specifically provided according to the invention for recombination purposes, either as isolated invasion plasmid or for in situ recombination.

The term "essential" as used herein with respect to a gene is understood to refer to a gene necessary for a living organism to survive, e.g. for a bacterial cell to replicate. Mutation of an essential gene, such as a deletion and/or inactivation, would cause a lethal phenotype or a non-replicable cell. Essential genes of *Shigella* may be mutated to delete the gene(s) of the *Shigella* chromosome, and further to incorporate the gene(s) into the invasion plasmid to stabilize the invasion plasmid. This provides for cultivation of a *Shigella* with a stable recombinant endogenous invasion plasmid. Among the essential genes of *Shigella* there are the ppa, accD, acpS, dapE, era, frr, ftsI, ftsL, ftsN, ftsZ, infA, lgt, IpxC, msbA, murA, murI, nadE, parC, proS, pyrB, rpsB, trmA, rho and rhoL genes.

Herein "inactivation" of a gene is always understood to refer to transient, inducible or constitutive down-modulation of a gene, so to reduce or inhibit expression of a gene product. This may specifically be done by mutation of a gene or regulatory sequence operably linked to the gene, such as promoters, enhancers, etc. that regulate the expression of a gene. Among the inactivating mutations there are particularly those that result in the reduction or suppression of expression of polynucleotides or genes, e.g. genes encoding virulence factors, or lead to the expression of respective non-functional proteins, e.g. non-functional virulence factors.

The term "invasive" or "non-invasive" as used herein with respect to a gene is understood in the following way. Invasive pathogenic bacteria are capable of invading eukaryotic cells. For example, after invasion, *Shigella* may multiply intracellularly and spread to neighbouring epithelial cells, resulting in tissue destruction and characteristic pathology of Shigellosis. Among the genes mediating invasiveness of *Shigella* there are e.g. the ipa genes encoding invasion plasmid antigens. Deletion and/or inactivation of at least one of such genes may lead to a non-invasive *Shigella*.

The Sereny test is a standard test for determining the invasiveness of organisms such as *Shigella* or *Escherichia coli*. (Wood et al. J. Clin. Microbiol. 24: 498-500, 1986). It is done by inoculating suspension of bacteria into guinea pig's eye. Severe mucopurulent conjunctivitis and severe keratitis indicates a positive test.

The term "isolated" or "isolation" as used herein with respect to a nucleic acid, and in particular with respect to a vector, plasmid and specifically the invasion plasmid of *Shigella*, shall refer to such compound that has been sufficiently separated from the environment with which it would naturally be associated, so as to exist in "substantially pure" form. The term "substantially pure" or "purified" as used herein shall refer to a preparation comprising at least 50% (w/w), preferably at least 60%, 70%, 80%, 90% or 95% of a compound, such as a nucleic acid molecule or a plasmid. Purity is measured by methods appropriate for the compound (e.g. chromatographic methods, polyacrylamide gel electrophoresis, HPLC analysis, and the like).

"Isolated" does not necessarily mean the exclusion of artificial or synthetic mixtures with other compounds or materials, or the presence of impurities that do not interfere with the fundamental activity, and that may be present, for example, due to incomplete purification. In particular, isolated nucleic acid molecules of the present invention are also meant to include those chemically synthesized.

With reference to the isolated invasion plasmid of the invention, this term refers to a plasmid that is separated from the cytoplasm in which it originated. An "isolated plasmid" may further represent a plasmid produced directly by biological or synthetic means and separated from other components present during its production.

The term "mutagenesis" with respect to a gene as used herein shall mean the mutation of a genetic sequence, in particular any of deletion, substitution, insertion of at least one nucleotide, or any combinations thereof, to obtain a mutated gene. This shall particularly refer to entire gene(s) or a significant part thereof, e.g. a deletion of at least 50% of the gene. The terms "mutagenesis" and "mutation" are herein used interchangeably.

The term "rough" with respect to a gram-negative bacteria, such as *Shigella*, means other than smooth, and shall specifically include "gently-rough" (i.e. O-ag synthesis downregulated) or "deep-rough" bacteria. The term "rough" as used herein may include characteristics such as an irregular colony morphology, and may include for instance undulate and/or lobate morphology. The term specifically means that a strain is unable and/or substantially unable to produce O-polysaccharide. A repetitive glycan polymer contained within an LPS is referred to as the O-antigen, O-polysaccharide, or O-(side-) chain of the bacteria. The O antigen is attached to the core oligosaccharide, and comprises the outermost domain of the LPS molecule. The presence or absence of the O-chains determine, whether the LPS is considered rough or smooth. Bacterial strains that have altered O-antigen structures change their appearance from smooth to dull when grown on agar plates. Full-length O-chains make the LPS smooth, while the absence or reduction of O-chains renders the LPS rough. "Smooth" bacteria include the complete core and O-antigen. "Rough" bacteria include a lack of LPS O-antigen, meaning no O-antigen or a reduced chain length of O-antigen or a reduced number of smooth LPS chains. The term "Gently-rough" refers to a subgroup of rough bacteria, which have a reduced chain length of O-antigen or a reduced number of smooth LPS chains. "Deep rough" bacteria have lost parts of the LPS core, consequently lack O-antigens as well.

The term "lack of LPS O-antigens" as used herein with respect to rough *Shigella* shall specifically refer to less than 50%, or less than 40%, or less than 30%, or less than 20%, or less than 10%, or essentially no or no LPS O-antigen as determined in a standard assay.

A standard test may be used to determine the rough characteristics of a strain.

For example, the phenotype of LPS mutants may e.g. be determined by SDS-PAGE separation of LPS and silver staining or agglutination tests using serotype-specific immune sera.

The rough *Shigella* may be produced by attenuation, e.g. by mutation of at least one gene or a significant part thereof, such as by deletion and/or inactivation, which gene is involved in the LPS synthesis, transport and/or expression, preferably selected from the group consisting of genes in the cluster of the rfb operon, or one or more of genes within the rfb/wbb gene cluster encoding O-antigen synthesis, waaL encoding the O-antigen ligase, wzx encoding O-antigen flippase involved in O-antigen transport, wzy/rfc involved in O-antigen polymerization, genes within the rfa/waa gene cluster encoding LPS-core synthesis, regulatory genes affecting O-antigen expression, such as rfaH, or loss of function(s) of which results in at least 90% reduction in the expression of O-antigens.

Specific examples of genes involved in the LPS sugar synthesis are rfbA, B, D and C.

Specific examples of genes involved in the LPS sugar transferase are rfbF and G.

A specific example of a gene involved in the LPS O-antigen polymerase is rfc/wzy.

The cluster of the rfb operon is located either on the chromosome or on the invasion plasmid (*Shigella sonnei*). Specific genes in this cluster are rfb F, D, C, E, J and/or I genes.

As used herein, the term "recombinant" refers to a molecule or construct that does not naturally occur in a host cell. In some embodiments, recombinant nucleic acid molecules contain two or more naturally-occurring sequences that are linked together in a way that does not occur naturally. A recombinant protein refers to a protein that is encoded and/or expressed by a recombinant nucleic acid. In some embodiments, "recombinant cells" express genes that are not found in identical form within the native (i.e., non-recombinant) form of the cell and/or express native genes that are otherwise abnormally over-expressed, under-expressed, and/or not expressed at all due to deliberate human intervention. Recombinant cells contain at least one recombinant polynucleotide or polypeptide. "Recombination", "recombining", and generating a "recombined" nucleic acid generally encompass the assembly of at least two nucleic acid fragments. In certain embodiments, recombinant proteins and recombinant nucleic acids remain functional, i.e., retain their activity or exhibit an enhanced activity in the host cell. In any case an attenuated bacterium, such as the attenuated *Shigella* of the invention is considered a recombinant cell. A nucleic acid construct, such as a plasmid or vector, nucleic acid (e.g., a polynucleotide), polypeptide, or host cell is referred to herein as "recombinant" when it is non-naturally occurring, artificial or engineered. A recombinant invasion plasmid of *Shigella* is particularly engineered to incorporate a specific deletion and/or inactivation of one, two or more poly-nucleotide(s) or genes, such as at least one deletion of genes encoding invasion plasmid antigens, and/or further comprises one or more heterologous genes, such as genes encoding protective antigens.

A "stable" recombinant invasion plasmid of *Shigella* is a *Shigella* plasmid that displays at least 50%, at least 60%, at least 70%, at least 80%, at least 90%, or greater than 90% retention in a *Shigella* cell culture under conditions selected to maintain the plasmid in the cell culture. A specific example of a stable recombinant invasion plasmid of *Shigella* refers to a recombinant *Shigella* host cell that has been mutated to delete and/or inactivate an essential gene located at a chromosomal locus, and integrated at a locus of the invasion plasmid. While a *Shigella* without the invasion plasmid would not grow or not be replicated, the *Shigella* bearing the endogenous invasion plasmid would be able to grow and replicate in vivo.

As used herein, the term "vector" refers to a vehicle by which a DNA or RNA sequence, e.g. a foreign (heterologous) gene, can be introduced into a host cell, so as to transform the host and promote expression (e.g. transcription and translation) of the introduced sequence. Plasmids are preferred vectors of the invention, in particular the invasion plasmid of *Shigella*, including specifically an endogeneous invasion plasmid.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin; that can readily accept additional (foreign) DNA and which can readily introduced into a suitable host cell.

The *Shigella* of the present invention preferably comprises the recombinant endogenous invasion plasmid used as a vector to express one or more heterologous genes. Thus, according to a preferred embodiment, the *Shigella* is a "no artificial vector" strain, meaning that the strain does not comprise an artificial plasmid, besides any (recombinant) endogenous plasmid.

A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors will often include one or more replication systems for cloning or expression, one or more markers for selection in the host, e.g. antibiotic resistance, and one or more expression cassettes. The term "expression system" means a host cell and compatible vector under suitable conditions, e.g. for the expression of a protein coded for by foreign DNA carried by the vector and introduced to the host cell.

Therefore, the attenuated *Shigella* according to the invention is specifically used in the development of a live vaccine.

The attenuated *Shigella* specifically is derived from a virulent strain of any of the *Shigella* species and serogroups (serotypes). For example, any of the following groups:

Serogroup A: *S. dysenteriae* (12 serotypes)
Serogroup B: *S. flexneri* (15 serotypes and subserotypes)
Serogroup C: *S. boydii* (18 serotypes)
Serogroup D: *S. sonnei* (1 serotype)

The virulent *Shigella* strain as used herein for the purpose of attenuation may be a clinically known virulent strain or a strain that is identified as containing virulence factors. Specifically the strain is selected from any of *S. flexneri, S. sonnei, S. dysenteriae* and *S. boydii*, in particular *S. flexneri* 2a, such as *S. flexneri* 2a 2457T (ATCC 700930, DNA=700930D-5), or CIP 107659 (Institute Pasteur, France).

The virulent *Shigella* strain may be modified by methods known in the art including multiple serial passage, temperature sensitive attenuation, mutation, or the like such that the resultant strain is attenuated, specifically avirulent, not capable of causing disease in a subject.

In some embodiments, the modification to the virulent strain results in the deletion and/or inactivation of a gene, including reduction or suppression of expression of polynucleotides or genes encoding virulence factors or leads to the expression of non-functional virulence factors.

There are a number of techniques well known in the art to obtain attenuating mutations, e.g. for reducing or abolishing polynucleotide expression. For example, a mutation may be introduced at a predetermined site, such as the promoter region or within the coding sequence to produce a nonsense mutation, using recombinant DNA-technology. Recombinant DNA techniques comprise cloning the gene of interest, modification of the gene sequence by site-directed mutagenesis, restriction enzyme digestion followed by re-ligation and subsequent replacement of the wild type gene with the mutant gene.

Suitable standard recombinant DNA techniques are known in the art and described inter alia in Sambrook et al., "Molecular Cloning: A Laboratory Manual" (1989), 2nd Edition (Cold Spring Harbor Laboratory press).

The attenuating mutations may be performed employing methods well-known in the art, including cloning the DNA sequence of the wild-type gene into a vector, e.g. a plasmid, optionally inserting a selectable marker into the cloned DNA sequence or deleting a part of the DNA sequence, resulting in its inactivation. A deletion may be introduced by, for example, cutting the DNA sequence using restriction enzymes that cut at two points in or just outside the coding sequence and ligating together the two ends in the remaining sequence. Alternatively, a mutant allele in which the flanking regions of a target gene are amplified separately and linked directly together in a separate overlap PCR reaction, with omission of the intervening target sequence, can be constructed. A plasmid carrying the mutated DNA sequence can be transformed into the bacterium by known techniques such as electroporation chemical trans-formation or conjugation. It is then possible by suitable selection to identify a mutant wherein the inactivated DNA sequence has recombined into the chromosome of the bacterium and the wild-type DNA sequence has been rendered non-functional by homologous recombination.

Furthermore, if an antibiotic resistance gene was used, it is generally removed from the bacteria before they are used in a vaccine. According to the method of Datsenko et al. (Proc. Natl. Acad. Sci. U.S.A 97, 6640-6645 (2000)) mutagenesis is based on the lambda bacteriophage Red recombinase system that allows specific disruption of both plasmid encoded and chromosomal genes. The strategy is to replace such genes, e.g. with a selectable antibiotic resistance gene, which is generated by PCR using primers with 40-60 nt homology extensions to the targeted gene. The Red-based recombination is mediated in these homologous sequences. Following selection, the antibiotic resistance gene can also be eliminated using a helper vector that expresses the FLP recombinase, which uses FRT direct repeats (FLP recognition target) flanking the antibiotic resistance gene.

In some embodiments, a mutation may be introduced at a predetermined site in chromosomal or extrachromosomal DNA, e.g. a plasmid, via an insertion, a deletion, or a substitution of one nucleotide by another, such as a point mutation, which leads to a mutated gene that has reduced or no expression. The mutation should produce a *Shigella* strain that has a reduced capacity to cause dysentery. Preferably, the mutation is a deletion mutation, where disruption of the gene is caused by the excision of nucleic acids. Such a mutation can, for example, be made by the deletion of a contiguous span of base pairs. Even very small deletions such as stretches of 10 base pairs can cause the gene to encode no protein or a non-functional protein. Even the deletion of one single base pair may lead to no protein or a non-functional protein, since as a result of such a mutation, the other base pairs are no longer in the correct reading frame or transcription has been inhibited or diminished. More preferably, a longer stretch is removed e.g. 100 base pairs or at least the significant part of a gene, e.g. at least 50% of the gene. Even more preferably, the whole gene is deleted.

Well-defined and deliberately made mutations involving the deletion of fragments or the whole gene, or combinations thereof, have the advantage, in comparison to classically induced mutations, that they will not revert to wild-type. Thus, in some embodiments of the invention the vaccine strain comprises a live attenuated *Shigella* strain in which a mutation in a gene encoding a virulence factor comprises a deletion or an insertion to disrupt the polynucleotide sequence encoding the virulence factor so that no corresponding protein is produced or the protein is non-functional.

Exemplary virulence factors selected to engineer an attenuated *Shigella* strain are rib, ipaB, ipaC or aroC.

The attenuation may, for example, be brought about by deleting and/or inactivating one or more of the following genes, or (a significant) part thereof, or any of the modulators of said gene effecting attenuation of said genes: rfb, aroA, aroC, aroD, aroE, virG and ipaA-D. Preferred attenuated *Shigella* strains of the invention are double mutants or multiple mutant strains with at least three or more attenuating mutations. Preferred combinations of target genes for attenuating mutations include at least one rfb gene (e.g. rfb F, D, C, E, J and/or I genes) and at least one ipa gene (e.g. ipaB, ipaC).

As an alternative to attenuating mutations resulting from genetic engineering, it would also be possible to identify naturally occurring strains of *Shigella* that are avirulent or comprise one or more preexisting mutations in a polynucleotide or gene encoding a virulence factor which can be used as live vaccine strains. These naturally occurring *Shigella* strains, once isolated by standard techniques, may be subjected to further mutagenesis or recombinant DNA techniques to construct double or multiple mutant strains.

Techniques for identifying bacteria that have one or more mutations in genes encoding virulence factors are known by one skilled in the art. Accordingly, routine techniques for the detection of *Shigella* strains that have been mutated by the techniques described above include Northern and Western blotting, PCR, ELISAs and cytotoxicity assays as described elsewhere herein. Mutant strains with no functional genes encoding specific virulence factors can easily be selected employing standard techniques.

Genes encoding the virulence factors to be attenuated may be plasmid-borne. Therefore, in some embodiments the modification to a virulent *Shigella* strain comprises mutating one or more endogenous *Shigella* plasmids. The term "plasmid", specifically refers to cytoplasmic DNA that replicates independently of the bacterial chromosome. The mutation of parts of the *Shigella* virulence or invasion plasmid or even the elimination of a plasmid may be envisaged. However, it is preferred that the attenuated *Shigella* still comprises the endogenous invasion plasmid, more preferable a stable invasion plasmid. This ensures the stability of the attenuated strain, in particular with respect to the potential loss of the invasion plasmid by the attenuated cell, or the potential uptake of a (native) invasion plasmid derived from a wild-type *Shigella*, which may occur with an instable strain or instable invasion plasmid.

The *Shigella* invasion plasmid is endogenous in most strains of *Shigella*. Though the invasion plasmid may be lost on cultivating a *Shigella* strain, it may be engineered to obtain a recombinant one exhibiting a high level of stability, which renders it an attractive target for development as a useful vector to incorporate heterologous genes encoding antigens, in particular protective antigens.

The recombinant invasion plasmid of the present invention obtained in the examples described hereinafter has the features as indicated in FIGS. 5 and 10A.

The plasmid of the present invention includes derivatives thereof autonomously replicable in *Shigella*. Such a derivative may be one corresponding to the invasion plasmid of which portion other than the region responsible for the invasion is removed therefrom, or one corresponding to the invasion plasmid of which part is inserted with another (heterologous) DNA sequence. Thereby a suitable shuttle vector autonomously replicable in *Shigella* may be obtained. Such vector may be used in any of the attenuated *Shigella* live vaccine strains according to the invention, or in any other bacteria capable of incorporating an invasion plasmid, including enteroinvasive *Escherichia*.

The endogenous *Shigella* invasion plasmid is well characterized in the art, and this knowledge informs selection of sites for recombination in such plasmids, as well as appropriate propagation conditions, e.g. at position between ntds 103187-103328 between an 15100 and ipaJ genes (these positions are determined for the pCP301 invasion plasmid of the *Shigella flexneri* 2a 301 strain)

The plasmid preferably is employed as a single copy plasmid.

The plasmid of the present invention may be provided in the isolated form, e.g. by preparing a DNA fraction of cytoplasm from the *Shigella* cells by a common method for preparing a plasmid DNA from cells. Further, the DNA fraction may be purified by density-gradient centrifugation method, agarose gel electrophoresis and the like.

For the construction of a shuttle vector, the whole sequence or a part thereof may be used. When a part thereof is used, such a part typically contains the region responsible for the replication of the plasmid, but a region unnecessary for the replication may be excluded. For example, the region required for the replication can be determined by ligating a part obtained by digesting the plasmid with a restriction enzyme to a plasmid autonomously replicable in *Shigella*, transforming another bacterium, such as another *Shigella* strain or an *Escherichia* strain, with the obtained recombinant plasmid, and determining if the recombinant plasmid is harbored by the transformant.

The vaccine according to the invention may be formulated using known techniques for formulating attenuated bacterial vaccines. The vaccine is advantageously presented for oral administration, for example as an aqueous solution or dried powder for reconstitution in a suitable buffer prior to administration. Reconstitution is advantageously effected in a buffer at a suitable pH to ensure the viability of the bacteria. In order to protect the attenuated bacteria and the vaccine from gastric acidity, a protective agent, such as sodium bicarbonate is advantageously administered with each administration of the vaccine. Alternatively the vaccine is presented in a lyophilized encapsulated form.

Vaccine strains may be administered in a pharmaceutically acceptable vehicle, e.g. as a spray or mixed in food and/or water or delivered in admixture with a suitable carrier, diluent, adjuvant or excipient such as sterile water, physiological saline, glucose, or the like. The vaccine strains may contain auxiliary substances such as wetting or emulsifying agents, pH buffering agents, adjuvants, gelling or viscosity enhancing additives, preservatives, flavoring agents, colours, and the like, depending upon the route of administration and the preparation desired. Pharmaceutical carriers for preparation of pharmaceutical compositions and medicaments are well known in the art, as set out in textbooks such as "Remington's Pharmaceutical Sciences" (1990), 18th Edition (Mack Publishing Co.).

The vaccine strains of the present invention can be administered in dosages and by techniques well known to those skilled in the medical or veterinary arts, taking into consideration such factors as the age, sex, weight, species and condition of the recipient subject, and the route of administration. The route of administration can be percutaneous, via mucosal administration (e.g., oral, nasal, anal, vaginal) or via a parenteral route (intradermal, intramuscular, subcutaneous, intravenous, or intra-peritoneal). Vaccine strains can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions.

The vaccine may be used in the vaccination of a subject, particularly a human being, or else a warm-blooded mammalian, specifically including pigs.

Once produced the vaccine strain of the present invention may be administered to a subject in the course of an active immunotherapy, specifically by vaccination, to prevent enteral disease, specifically dysentery caused by *Shigella* and optionally heterologous enteral or diarrheal pathogens. This may be achieved by any of the vaccines according to the invention, which are cross-protective and/or polyvalent.

An infection caused by *Shigella* and optionally other a microorganism, such as diarrheal microorganisms targeted by a cross-protective and/or polyvalent vaccine of the invention, may therefore be prevented or treated by administering an effective dose of the vaccine according to the invention. The dosage employed may ultimately be at the discretion of the physician, but will be dependent on various factors including the size and weight of the subject and the type of vaccine formulated. However, a dosage comprising the oral administration of from $10^7$ to $10^{11}$, e.g. from $10^8$ to $10^{10}$, bacteria per dose may be convenient for a 70 kg adult human host.

An infection caused by *Shigella* and optionally other a microorganism, especially a pathogen, may therefore be prevented or treated by administering an effective dose of a vaccine according to the invention. The dosage employed may ultimately be at the discretion of the physician, but will be dependent on various factors including the size and weight of the subject and the type of vaccine formulated. However, a dosage comprising the oral administration of from $10^7$ to $10^{11}$, e.g. from $10^8$ to $10^{10}$, bacteria per dose may be convenient for a 70 kg adult human host.

According to specific examples, isogenic attenuated mutants of a prototype S. flexneri 2a strain were constructed. The mutants were either unable to synthesize O-antigens (ΔrfbF) or—representing a well-proven vaccine approach—were auxotrophic (ΔaroC). Virulence of these mutants in the mouse lung model showed a comparable level of attenuation. Subsequently, we isolated derivatives of both mutants that lacked the invasion plasmid encoding the Ipa-s (Congo red negative/CRN/mutants). Loss of the invasive phenotype in these latter mutants increased attenuation further to an undetectable level. This series of S. flexneri 2a mutants lacking either O-antigens (ΔrfbF CRP), or ipa proteins (ΔaroC CRN), or both (ΔrfbF CRN) or none of these antigens (ΔaroC CRP) were used to immunize mice at sublethal doses intranasally. Subsequently, mice were challenged by lethal doses of heterologous S. flexneri 6 (FIG. 1a) or S. sonnei (FIG. 1b) wild type strains. The attenuated mutant expressing both ipa and O-antigens (ΔaroC CRP) could not provide protection over the level observed at mock vaccinated mice. In contrast, the double mutant lacking both major immunogenic groups of antigens elicited high protection against both heterologous challenge strains. Even loss of the virulence plasmid alone (ΔaroC CRN) appeared to improve cross-protection. In order to corroborate these results, groups of mice were also immunized with Phase I (Ipa and O-antigen positive) and Phase II (Ipa and O-antigen negative) variants of a S. sonnei isolate. The Phase II vaccine strain provided high protection against a challenge by S. flexneri 6, whereas immunization with the fully virulent Phase I strain afforded no significantly different survival from that provided by saline (FIG. 1c).

To support the concept that improved cross-protection originates from increased immunogenicity of minor antigens at this mutant backgrounds (i.e. upon the loss of dominant antigens—see FIG. 2), immune reactivity of serum and bronchoalveolar lavage (BAL) samples obtained from the immunized mice were compared in ELISA on whole bacterial cells that expressed both or none of the major antigenic groups (FIG. 3).

BAL obtained from mice vaccinated with the ΔaroC CRP (both ipa and O-antigen positive) mutant were more reactogenic to the invasive smooth homologous target verifying that these antigens, indeed, dominated the immune response. On the contrary, loss of the immunodominant antigens on the vaccine strain (ΔrfbF CRN) resulted in an improved reactogenicity to the homologous target strain devoid of both O- and Ipa antigens.

Furthermore, the heterologous S. sonnei strain was more readily recognized by BAL obtained from mice vaccinated by the double mutant. These results corroborate that there is a higher titer of mucosal antibodies against those shared minor antigens that are accessible on these targets. Interestingly, this phenomenon was not apparent in case of serum IgG (data not shown), supporting earlier findings showing that sIgA rather than serum IgG mediates protection in this model.

Current vaccine approaches (in general as well as to Shigella in particular) rely on the utilization of major immunogenic antigens. In order to evade the immune response, however, evolutionary pressure has selected multiple immunologically distinct variants of these antigens, which form the basis of classifying pathogens in serotypes. Utilization of serotype-determining major antigens might therefore confer only partial protection against a pathogen, unless all serotypes can be included in the vaccine (e.g. in case of poliovirus vaccines). Combination of the most prevalent serotypes can give a relatively broad protection, however, this could be transient due to serotype replacement (i.e. less common serotypes emerge filling the gap opened by the eradication of the vaccine serotypes). This necessitates vaccine optimization from time to time, for example by including additional serotypes in the multivalent vaccines. Due to phenomena like antigenic competition and interference as well as financial considerations, however, the maximum number of serotypes to be covered is limited.

On the other hand, various serotypes of a given bacterial pathogen share a huge number of conserved antigens on their surface. The fact that they could have remained conserved implies that they are either not accessible on the surface (not protective antigens) and/or their function is so indispensible for pathogenesis that allows no modification in their antigenic structure. This is exemplified by the Shigella ipa proteins, which are highly conserved (due to their sophisticated function in invasion) and very immunogenic, still can not elicit cross-protection, probably because they are only expressed upon contact to the target cell, hence probably not accessible for an antibody-mediated protective mechanism.

Specifically we show (FIG. 2.), that immunodominant antigens such as Ipa and O antigens hijack the immune response in a way that allows less antibodies to be raised against minor antigens. Given that Ipa-s are not protective and O-antigens are highly variable, Shigella can efficiently evade the immune response. We show, however, that deletion of these classes of antigens highly improved cross-protective potential of live vaccine strains.

As regards the invasion plasmid mutation, instead of selection for spontaneous deletion mutant of the invasion plasmid based on the loss of Congo Red positivity, the ipaB and C genes may be removed, while the rest of the plasmid is intact.

Moreover, the plasmid may be stabilized by implantation of an essential gene, such as ppa, from the chromosome to the invasion plasmid.

Furthermore, the expression of foreign (heterologous) antigens, such as ETEC LTB and mutated STa (STm) toxins are feasible. STm preferably contains one or more point mutations. Specifically preferred STm are (SEQ ID 1)
NSSNYCCELCCXXACTGCY, wherein
X at position 12 is N, K or R, and/or
X at position 13 is P, G, L or F,
wherein the STm excludes the wild-type sequence:

(SEQ ID 2)
NSSNYCCELCCNPACTGCY.

Preferred combinations of point mutations are N12K or N12R in combination with P13F.

Furthermore, examples show that relative immunogenicity of shared conserved antigens had increased in the absence of the major antigens in the vaccine strain. As these deletions not only improve the spectrum of protection but also render the vaccine strain highly avirulent, the double mutant is considered as very safe, even at extremely high doses. Moreover, live oral vaccines are relatively cheap to manufacture, and require no trained medical personnel for administration, which are important factors when considering the target population in endemic countries.

The subject matter of the following definitions is considered embodiments of the present invention:

1. A live attenuated *Shigella* vaccine, which is based on a rough *Shigella* strain lacking LPS O antigen, preferably a non-invasive strain.

2. Vaccine according to definition 1, which is attenuated by mutagenesis of one or more genes involved in the LPS synthesis, transport and expression, preferably selected from the group consisting of genes in the cluster of the rfb or one or more genes within the rfb/wbb gene cluster encoding O-antigen synthesis, waaL encoding the O-antigen ligase, wzx encoding O-antigen flippase involved in O-antigen transport, wzy/rfc involved in O-antigen polymerization, genes within the rfa/waa gene cluster encoding LPS-core synthesis, regulatory genes affecting O-antigen expression, such as rfaH, or loss of function(s) of which results in at least 90% reduction in the expression of O-antigens.

3. Vaccine according to definition 1 or 2, wherein said mutagenesis is by a deletion of one or more of the rfb F, D, C, E, J and/or I genes, or a deletion of a part thereof, or corresponding genes in various *Shigella* serotypes.

4. Vaccine according to any of definitions 1 to 3, wherein said *Shigella* strain is selected from the genus *Shigella*, e.g. from any *Shigella* serotype or species, in particular *S. flexneri*, *S. sonnei*, *S. dysentheriae* and *S. boydii*.

5. Vaccine according to any of definitions 1 to 4, wherein said *Shigella* expresses cross-reactive outer membrane proteins.

6. Vaccine according to any of definitions 1 to 5, which is cross-protective against different serotypes and species of *Shigella*, in particular against any of *S. flexneri* 2a, *S. flexneri* 6 and *S. sonnei*, or enterinvasive *Escherichia coli*.

7. Vaccine according to any of definitions 1 to 6, wherein said *Shigella* is non-invasive by further mutagenesis of the invasion plasmid, in particular a deletion of the ipaB and/or ipaC genes and/or other ipa genes.

8. Vaccine according to any of definitions 1 to 7, wherein said *Shigella* comprises a recombinant endogenous invasion plasmid incorporating at least one gene encoding a heterologous antigen to secrete said antigen or to express said antigen, e.g. on the bacterial cell surface.

9. Vaccine according to definition 8, wherein said antigen is selected from the group consisting of
 a bacterial antigen preferably a toxin or colonization factor,
 a viral antigen, preferably from a pathogen causing enteral or mucosal infections,
 a fungal antigen, preferably from a pathogen causing enteral or mucosal infections, and
 a parasitic antigen, preferably from a pathogen causing enteral infections.

10. Vaccine according to definition 9, wherein the bacterial antigen is originating from enteropathogenic bacteria, preferably selected from the group consisting of
 a. *E. coli* antigens, in particular an enterotoxin selected from the group consisting of LTB, mutated LTA and ST of ETEC, subunits, or fusions thereof, antigens from enteroaggregative *E. coli* (EAEC), or Shiga-like toxin 1 or 2
 b. *Campylobacter jejuni* antigens,
 c. *Clostridium difficile* antigens, specifically toxins A and B d. *Vibrio cholera* antigens, specifically the CT-B antigen, and
 e. mutants or fusion proteins of a), b) c) or d).

11. Vaccine according to definition 10, wherein said ETEC is a fusion enterotoxin of LTB and mutant ST (STm), in particular a fusion protein comprising an STm with an amino acid sequence as shown in SEQ ID 1.

12. Vaccine according to definition 10, wherein the viral antigen is originating from diarrheal viruses, preferably selected from the group consisting of rotaviruses and caliciviruses, such as Norwalk virus.

13. Vaccine according to definition 10, wherein the parasite antigen is originating from diarrhea-causing protozoa, preferably selected from the group consisting of *Giardia lamblia*, *Cryptosporidium* species and *Entameba histolytica*

14. Vaccine according to definition 10, wherein the fungal antigen is originating from diarrhea-causing fungi, preferably selected from the group consisting of *Blastomyces dermatiditis* and *Histoplasma* spp.

15. Vaccine according to any of definitions 1 to 14, wherein said *Shigella* further comprises a deletion of an essential chromosomal gene and an insertion of said gene into the invasion plasmid, in particular the ppa gene or any of accD, acpS, dapE, era, frr, ftsI, ftsL, ftsN, ftsZ, infA, lgt, lpxC, msbA, murA, murI, nadE, parC, proS, pyrB, rpsB, trmA, rho and rhoL.

16. Vaccine according to any of definitions 1 to 15, for use in the active immunotherapy of a subject to prevent infectious diseases, in particular enteral disease, such as diarrheal or dysentery disease.

17. Vaccine for use according to definition 16, wherein said enteral disease is caused by any *Shigella* serotype or species.

18. Vaccine for use according to definition 16 or 17, wherein the immunotherapy comprises administration of the vaccine in a mucosal or oral formulation.

19. Vaccine for use according to any of definitions 16 to 18, wherein the vaccine is administered orally or intranasally.

20. Vaccine for use according to any of definitions 16 to 19, wherein
 a polyvalent vaccine is used expressing protective antigens of *Shigella* and at least one pathogen of a species other than *Shigella* by the incorporation of a protective antigen of said pathogen into the endogenous invasion plasmid, and wherein
 said infectious disease is caused by any *Shigella* serotype or species and/or said pathogen.

21. *Shigella* strain, which is a *S. flexneri* 2a strain with a deletion of the rfbF, ipaB and/or ipaC genes, or a deletion of essential parts thereof.

22. *Shigella* strain according to definition 21, which comprises a recombinant invasion plasmid incorporating at least one gene encoding a heterologous antigen to express said antigen or secrete said antigen.

23. *Shigella* strain according to definition 21 or 22, which further comprises a deletion of an essential chromosomal gene and an insertion of said gene into the invasion plasmid.

24. A recombinant plasmid vector based on a mutated *Shigella* invasion plasmid comprising a nucleotide sequence encoding at least one heterologous antigen, wherein the plasmid is mutated in at least one of the ipaB and/or ipaC genes.

25. Bacterial host cell comprising the vector according to definition 24, wherein said host cell is selected from the genera *Shigella*, *Escherichia*, *Salmonella*, *Campylobacter* or *Yersinia*.

26. Host cell according to definition 25, wherein the vector is an endogenous invasion plasmid.

The foregoing description will be more fully understood with reference to the following examples. Such examples are, however, merely representative of methods of practicing one or more embodiments of the present invention and should not be read as limiting the scope of invention.

EXAMPLES

Example 1: Preparation of an Attenuated *Shigella* Strain

Methods

Bacterial Strains and Culture Conditions

Bacteria were routinely grown in Luria Bertani (LB) broth or agar plates. For the detection of an intact invasion plasmid expressing the ipa proteins tryptic soy agar (TSA) plates supplemented with 0.01% Congo Red dye (Sigma-Aldrich) were used. Fresh cultures were always started from a Congo Red-positive (CRP) colony ensuring plasmid carriage. Where appropriate media were supplemented by the following concentration of antibiotics: ampicillin 100 µg/ml, kanamicin 100 ug/ml, chloramphenicol 25 µg/ml.

The sequenced prototype *Shigella flexneri* 2a strain 2 (strain 2457T, ATCC 700930) was used as a parental strain for mutagenesis. Inactivation of the aroC and rfbF genes was performed by the Red recombinase technique described earlier (Levine, M. M., et al. Nat. Rev. Microbiol. 5, 540-553 (2007)). Deletion of aroC results in an auxotrophic mutant unable to synthesize aromatic compounds. RfbF is involved in the synthesis of the O-antigen subunits, loss of which results in a rough LPS phenotype. The oligonucleotides used for the generation and confirmation of the mutations are provided as Supplementary Table 1 in FIG. 4 (SEQ ID 3-10). Mutants 2457TΔaroC::kan and 2457TΔrfbF::cat were subsequently cultured on Congo Red (CR) agar plates to select CR-positive (CRP) and CR-negative (CRN) colonies. The loss of virulence determinants encoded on the invasion plasmid was confirmed by PCR. Similarly, phase I and phase II variants of *S. sonnei* were differentiated on CR plates. Phase I is the traditional designation of invasion plasmid-bearing wild-type *S. sonnei* strains, whereas phase II refers to plasmid-lost strains. As O-antigen synthesis is also encoded on the virulence plasmid in this species, phase II variants are both non-invasive and rough. The wild-type *Shigella flexneri* 6 and *S. sonnei* strains used for the challenge studies had been isolated from clinical cases of bacillary dysentery. Their serotypes were determined by slide agglutination using commercial typing sera (Mast Assure™; Mast Group Ltd., Merseyside, UK).

Animal Experiments

All in vivo studies were performed in the formerly described mouse lung model (van de Verg et al., Infect Immun 63: 1947-1954, 1995). 6-8 weeks old female BALB/c mice were anesthetised intraperitoneally with a mixture of 5 mg/ml ketamine (Calipsol, Richter Gedeon, Hungary) and 0.3 mg/ml xilazine (Primasine, Alfasan).

Infections were performed intranasally with 50 µl of inoculum (diluted in saline) containing the required CFU of bacteria. Bacterial counts were justified by plating of serial dilutions from the inocula. 50 percent lethality doses (LD50 values) were calculated from infections by 0.5 log-serial dilutions ($10^5$-$10^8$ CFU) according to Reed and Muench (Oaks, E V, et al. Infect. Immun. 53: 57-63, 1986). Vaccinations were done with sub-lethal doses of bacteria ($10^6$ CFU of CRP mutants and $10^8$ cfu of CRN mutants from strain 2457T; $10^{5.5}$ CFU of phase I and $10^{7.5}$ CFU of phase II *S. sonnei*) two times with 2-week intervals. Control group received saline. In a pilot study it has been shown that all vaccine strains have been cleared within 3 days p.i. Two weeks after the booster immunization mice were challenged with a lethal dose of either the *S. flexneri* 6 or the *S. sonnei* wild-type strain.

Subsequently, lethality was monitored for 14 days. Alternatively, immunized mice were sacrificed two weeks after the booster and bronchoalveolar lavage (BAL) fluid and blood samples were collected. For the collection of BAL the trachea of euthanised mice was prepared for cannulation with a blunted needle and 200 µl saline was injected and retracted from the bronchi of each mouse.

ELISA

Bacteria inoculated from fresh CR plates were grown overnight in LB broth. 96-well plates (C.E.B., France) were coated overnight with 0.1 ml washed bacterial suspensions ($5 \times 10^8$ CFU/ml) in carbonate buffer (pH 9.5) at 4° C. The following day, plates were washed with PBS containing 0.05% Tween 20, and then blocked with PBS containing 2% BSA (Sigma-Aldrich) for 1 h at room temperature. BAL and serum samples were diluted in PBS containing 0.5% BSA and incubated with the antigen-coated plates for 1 h at 37° C. Serial dilutions were conducted across the plates. After three washes, plates were probed with anti-mouse IgG (for serum IgG) or anti-mouse IgA (for BAL samples) immunoglobulin conjugated with HRPO (Dako A/S, Denmark). The ELISA substrate was o-phenylenediamine (Sigma-Aldrich) dissolved in citric acid buffer containing $H_2O_2$. The OD was measured at 492 nm on a conventional ELISA plate reader. Immunoreactivity was expressed in relation to the reactivity of the Δaro CRP BAL sample at the same dilution (1:10). Means+SEM were calculated from 4 independent assays.

Statistical Analysis

The 50% lethality dose was calculated with the statistical method of Reed and Muench 6. The statistical analysis of the survival curves was performed with the LogRank (Mantel-Cox) test using GraphPad Prism version 5.00 for Windows. The IgA titers of BAL were compared with the Mann-Whitney non parametric analysis. The p value was considered significant if lower than 0.05.

Results

Based on the survival curves of animal immunized with the attenuated *Shigella flexneri* 2457T (serotype 2a) vaccine strains and challenged with the wild type *Shigella* strains, synergistic protective effect was observed by combining the rfbF gene deletion with the loss of invasion plasmid in the heterologous challenge setting. Significantly better protection was achieved by immunization with the Congo Red negative (CNR, with invasion plasmid deletion) *Shigella flexneri* 2457T (2a) ΔrfbF strain relative to that of the Congo Red positive (CNP, intact invasion plasmid) *Shigella flexneri* 2a ΔrfbF strain when the animals were challenged with the heterologous *Shigella flexneri* 6 strain (FIG. 1b). In case of homologous challenge with the wild type *Shigella flexneri* 544 strain (2a), both vaccine strains were equally protective, suggesting that for homologous challenge even the deletion of the rfbF gene is sufficient (FIG. 1a). The difference in vaccination efficacy is likely to be partially related to the higher allowable sub-lethal challenge dose with the ΔrfbF-invasion plasmid double mutant, but not fully accountable for, since the CRN Δaro (control) strain used at comparable challenge dose as the double mutant, induced partial protection in both homologous and heterologous challenge experiments (FIG. 1a,b).

Further evidence for the beneficial effect of mutations inactivating the rfbF gene and invasion plasmid achieving significant protection against heterologous challenge is provided by using *Shigella sonnei* vaccine strains. Immunization with the *Shigella sonnei* Phase II variant (deleted invasion plasmid responsible for expression of both the invasion complex and rfbF gene) afforded high level protection against lethal challenge with the wild type *Shigella flexneri* 542 strain (serotype 6), while the wild type *S. sonnei* strain phase I variant (intact invasion plasmid carrying the invasion complex and the rfbF gene) exhibited low (statistically not significant) protective effect (FIG. 1c).

Example 2: Preparation of *Shigella flexneri* 2a 2457 Mutant with Synthetic Gene Construct on the Invasion Plasmid The source material for mutant construction is the ATCC strain *Shigella flexneri* 2a 2457T as described above. Deletion of the rfbF and ipaB and ipaC genes as well as the ppa gene is performed using the Red recombinase technique (Datsenko, K. A. & Wanner, B. L. One-step inactivation of chromosomal genes in *Escherichia coli* K-12 using PCR products. *Proc. Natl. Acad. Sci. U.S.A* 97, 6640-6645 (2000)).

Step 1: the rfbF gene was removed from the chromosome. The lack of RfbF is associated with a phenotypic change: the *Shigella* strain becomes "rough", a typical morphological change that can be detected by naked eye on agar plates. This phenotypic change was observed, but the successful removal of the rfbF gene was also confirmed by PCR analysis. It was based on the different length of the PCR product obtained with genomic DNA from wild type or mutated *Shigella* (FIG. 8).

Step 2: the ipaB and ipaC genes were removed from the invasion plasmid. These genes are neighbors and were deleted together with the same Red recombinase technique applied to the rfbF gene deletion. This gene deletion also results in a phenotype: the *Shigella* loses the ability to take up the dye Congo Red and therefore forms a white colony on Congo Red containing agar plates in contrast to *Shigella* carrying the wild type plasmid which are red. Since *Shigella* can lose its plasmids spontaneously during in vitro culture, the deletion of the ipaB and ipaC genes was confirmed by PCR analysis of the mutants, and it was based on shorter PCR fragments obtained with the mutants, compared to the wild type plasmid (FIG. 9).

Figure 10B:
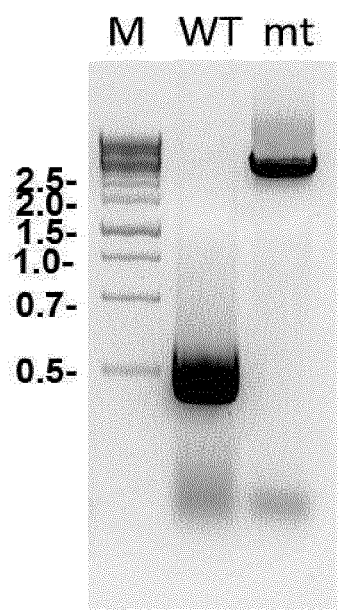
Figure 10C:
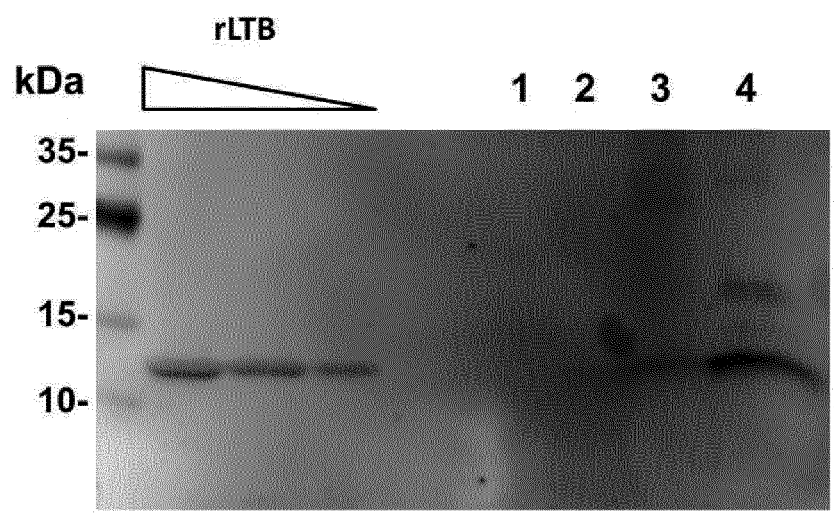

Step 3: Insertion of the synthetic gene that drives the expression of the ETEC toxins LT-B and ST, as well as transplants an essential gene (ppa) from the chromosome into the invasion plasmid (see FIG. 10A). The successful introduction of the LTB-mST fusion gene was proved by site specific PCR amplification of the region of genetic manipulation (FIG. 10B). Expression of the toxin fusion gene from *Shigella* was tested by immunoblotting (FIG. 10C). Removal of the ppa gene from the chromosome (essential for the growth of *Shigella*) was proved by PCR based on shorter length of amplicon from the final vaccine strain.

All genetic manipulations involved the insertion of antibiotic resistance genes. After each step the genes responsible for antibiotic resistance were removed with helper plasmids as described by Datsenko and Wanner (*Proc. Natl. Acad. Sci. U.S.A* 97, 6640-6645 (2000)).

Example 3: Animal Protection Studies to Test the Mutant Strain of Example 2

Virulence attenuation of the isogenic mutant strains vs. their parental wild-type strain was shown in the mouse lung model of shigellosis. Groups of mice were infected intranasally with 10-fold serial dilutions (between $10^6$ and $10^8$ cfu) of the different bacterial strains in order to determine the minimal lethal dose for each strains. In case of the wild-type strain, there was a 30, 50, and 100% lethality found at $10^6$, $10^7$, and $10^8$ cfu/mouse doses, respectively. In contrast, no mice died from any of the isogenic mutants 2457TΔrfb, 2457TΔipaBC, or double mutant 2457TΔrfbΔipaBC at any of the tested doses. These results suggest high virulence attenuation in all mutants upon deletion of the corresponding genes.

Subsequently, groups of mice were immunized in the same model with sublethal doses of either wild-type strain 2457T ($5 \times 10^6$ cfu/mouse) or its isogenic deletion mutants 2457TΔrfb, 2457TΔipaBC, 2457TΔrfbΔipaBC (all at $10^8$ cfu/mouse), or mock immunized with PBS only. Three identical immunizations were performed with 2-week intervals. One week following the last booster mice were challenged with a (previously optimized) lethal dose ($2 \times 10^6$ cfu/mouse) of a *S. sonnei* strain. As depicted on FIG. 11, immunization with the wild-type strain could not provide protection, whereas each of the single locus mutants (either 2457TΔrfb or 2457TΔipaBC) elicited partial protection, only. In contrast, the double mutant (2457TΔrfbΔipaBC) could provide full protection against infection by the heterologous *Shigella* species.

The invention claimed is:

1. A live attenuated *Shigella* vaccine comprising a non-invasive rough *Shigella* strain lacking LPS O-antigen, which is non-invasive by a mutation in the endogenous gene(s) in an endogenous invasion plasmid and is not capable of invading eukaryotic cells.

2. The vaccine according to claim 1, wherein the *Shigella* strain is selected from the group consisting of *S. flexneri, S. sonnei, S. dysentheriae* and *S. boydii*.

3. The vaccine according to claim 1, wherein the vaccine is cross-protective against different serotypes and species of *Shigella*.

4. The vaccine according to claim 3, wherein the species is selected from the group consisting of *S. flexneri* 2a, *S. flexneri* 6 and *S. sonnei*.

5. The vaccine according to claim 1, wherein the mutation comprises deletion of one or more ipa genes.

6. The vaccine according to claim 5, wherein the one or more ipa genes is ipaB and/or ipaC.

7. The vaccine according to claim 1, further comprising a mutation in one or more genes involved in LPS synthesis, transport and/or expression, wherein the mutation results in at least 90% reduction in the expression of the LPS O-antigen.

8. The vaccine according to claim 7, wherein the one or more genes are selected from the group consisting of genes in the cluster of the rib operon, genes within the rfblwbb gene cluster encoding O-antigen synthesis, waaL encoding the O-antigen ligase, wzx encoding O-antigen flippase involved in O-antigen transport, wzy/r/l involved in O-antigen polymerization, genes within the rfa/waa gene cluster encoding LPS-core synthesis, and regulatory genes affecting O-antigen expression.

9. The vaccine according to claim 8, wherein the regulatory gene affecting O-antigen expression is rfaH.

10. The vaccine according to claim 1, wherein the endogenous invasion plasmid is a recombinant endogenous invasion plasmid comprising at least one gene encoding a heterologous antigen to secrete said antigen or to express said antigen on the bacterial cell surface.

11. The vaccine according to claim 10, wherein said antigen is selected from the group consisting of a bacterial antigen, a viral antigen, a fungal antigen, and a parasitic antigen.

12. The vaccine according to claim 11, wherein the bacterial antigen is an enterotoxin of Enterotoxigenic *Escherichia coli* (ETEC) comprising the B subunit of heat labile toxin (LTB), the heat stable toxin (ST) or subunits or fusions thereof.

13. The vaccine according to claim 12, wherein said ETEC comprises LTB/STm, wherein STm comprises the amino acid sequence set forth in SEQ ID NO: 1.

14. The vaccine according to claim 1, wherein said *Shigella* strain further comprises a deletion of an essential chromosomal gene and an insertion of said gene into the endogenous invasion plasmid.

15. A method of preventing an infectious disease caused by *Shigella* in a subject, comprising administering to the subject in need thereof an effective amount of the vaccine according to claim 1.

16. The method according to claim 15, wherein the infectious disease is an enteral disease.

17. The method according to claim 16, wherein the vaccine is a polyvalent vaccine comprising protective antigens of *Shigella* and at least one pathogen of a species other than *Shigella*, and wherein said infectious disease or enteral disease is caused by any *Shigella* serotype or species and/or said pathogen.

18. The method according to claim 17, wherein the polyvalent vaccine comprises a protective antigen of said pathogen incorporated into the endogenous invasion plasmid.

19. The method according to claim 15, wherein the vaccine is administered orally or intranasally.

20. A method of preventing enteral disease caused by *Shigella* and/or *E. coli* in a subject comprising administering an effective amount of the vaccine according to claim 12.

21. An *S. flexneri* 2a strain comprising a deletion of the rjbF gene and deletion of at least one of the ipaB and/or ipaC genes.

22. An *S. flexneri* 2a strain according to claim 21, comprising a recombinant endogenous invasion plasmid having at least one gene encoding a heterologous antigen, wherein the gene expresses and/or secretes said antigen.

23. A mutated *Shigella* invasion recombinant plasmid vector comprising a mutation in an ipaB and/or ipaC genes, further comprising a nucleotide sequence encoding at least one antigen heterologous to *Shigella*, wherein said at least one antigen is selected from the group consisting of a bacterial antigen, a viral antigen, a fungal antigen and a parasitic antigen, wherein the *Shigella* is selected from the group consisting of *Shigella dysenteriae, Shigella flexneri, Shigella boydii*, and *Shigella sonnei*.

24. The recombinant plasmid vector of claim 23, wherein the vector is derived from *Shigella flexneri*.

25. The recombinant plasmid vector of claim 23, wherein the vector is derived from *Shigella flexneri* 2a.

26. The recombinant plasmid vector of claim 23, wherein the vector is derived from *Shigella flexneri* 2a 2457/T.

27. The recombinant plasmid vector of claim 23, wherein the vector is derived from *Shigella dysenteriae*.

28. The recombinant plasmid vector of claim 23, wherein the vector is derived from *Shigella boydii*.

29. The recombinant plasmid vector of claim 23, wherein the vector is derived from *Shigella sonnei*.

* * * * *

UNITED STATES PATENT AND TRADEMARK OFFICE
CERTIFICATE OF CORRECTION

PATENT NO. : 9,730,991 B2  
APPLICATION NO. : 14/426123  
DATED : August 15, 2017  
INVENTOR(S) : Gábor Nagy et al.

Page 1 of 1

It is certified that error appears in the above-identified patent and that said Letters Patent is hereby corrected as shown below:

In the Claims

Column 45, in Claims 5, 6, 8, 9: Line 17, "ipa" should read -- *ipa* --.
    Line 19, "ipa" should read -- *ipa* --.
    Line 19, "ipaB" should read -- *ipaB* --.
    Line 19, "ipaC" should read -- *ipaC* --.
    Line 27, "rib" should read -- *rfb* --.
    Line 27, "rfblwbb" should read -- *rfb/wbb* --.
    Line 30, "wzy/r/l" should read -- *wzy/rfc* --.
    Line 35, "rfaH" should read -- *rfaH* --.

Column 46, in Claims 21, 23, 26: Line 26, "rjbf" should read -- *rfbF* --.
    Line 26, "ipaB" should read -- *ipaB* --.
    Line 26, "ipaC" should read -- *ipaC* --.
    Line 33, "ipaB" should read -- *ipaB* --.
    Line 33, "ipaC" should read -- *ipaC* --.
    Line 46, "2457/T" should read -- 2457T --.

Signed and Sealed this
Twenty-fourth Day of April, 2018

Andrei Iancu
*Director of the United States Patent and Trademark Office*

SEQUENCE LISTING

```
<160> NUMBER OF SEQ ID NOS: 29

<210> SEQ ID NO 1
<211> LENGTH: 19
<212> TYPE: PRT
<213> ORGANISM: artificial
<220> FEATURE:
<223> OTHER INFORMATION: bacterial antigen
<220> FEATURE:
<221> NAME/KEY: PEPTIDE
<222> LOCATION: (12)..(12)
<223> OTHER INFORMATION: X can be N, K or R wherein Sequence
      NSSNYCCELCCNPACTGCY is excluded
<220> FEATURE:
<221> NAME/KEY: PEPTIDE
<222> LOCATION: (13)..(13)
<223> OTHER INFORMATION: X can be P, G, L or F, wherein Sequence
      NSSNYCCELCCNPACTGCY is excluded
```

<400> SEQUENCE: 1

Asn Ser Ser Asn Tyr Cys Cys Glu Leu Cys Cys Xaa Xaa Ala Cys Thr
1               5                   10                  15

Gly Cys Tyr

<210> SEQ ID NO 2
<211> LENGTH: 19
<212> TYPE: PRT
<213> ORGANISM: Escherichia Sp.

<400> SEQUENCE: 2

Asn Ser Ser Asn Tyr Cys Cys Glu Leu Cys Cys Asn Pro Ala Cys Thr
1               5                   10                  15

Gly Cys Tyr

<210> SEQ ID NO 3
<211> LENGTH: 63
<212> TYPE: DNA
<213> ORGANISM: artificial
<220> FEATURE:
<223> OTHER INFORMATION: Oligonucleotide

<400> SEQUENCE: 3
cgcacgggct ggcgctcggc tgctgcatcg tcgatggtgt tccgtgtagg ctggagctgc      60
ttc                                                                   63

<210> SEQ ID NO 4
<211> LENGTH: 70
<212> TYPE: DNA
<213> ORGANISM: artificial
<220> FEATURE:
<223> OTHER INFORMATION: Oligonucleotide

<400> SEQUENCE: 4
tatcagtctt cacatcggca ttttgcgccc gctgccgtaa catatgaata tcctccttag      60
ttcctattaa                                                            70

<210> SEQ ID NO 5
<211> LENGTH: 61
<212> TYPE: DNA
<213> ORGANISM: artificial
<220> FEATURE:
<223> OTHER INFORMATION: Oligonucleotide

<400> SEQUENCE: 5
gaatagtaat atttacgctg tcattgtgac atataatccc ggtgtaggct ggagctgctt      60
c                                                                     61

<210> SEQ ID NO 6
<211> LENGTH: 68
<212> TYPE: DNA
<213> ORGANISM: artificial
<220> FEATURE:
<223> OTHER INFORMATION: Oligonucleotide

<400> SEQUENCE: 6
gcattataac gaccgccccc agtaattcct cttattccca tatgaatatc ctccttagtt      60
cctaatcc                                                              68

<210> SEQ ID NO 7
<211> LENGTH: 22

```
<212> TYPE: DNA
<213> ORGANISM: artificial
<220> FEATURE:
<223> OTHER INFORMATION: Oligonucleotide

<400> SEQUENCE: 7
gagccgtgat ggctggaaac ac                                              22

<210> SEQ ID NO 8
<211> LENGTH: 22
<212> TYPE: DNA
<213> ORGANISM: artificial
<220> FEATURE:
<223> OTHER INFORMATION: Oligonucleotide

<400> SEQUENCE: 8
agcgcaatcg cggttttgtt ca                                              22

<210> SEQ ID NO 9
<211> LENGTH: 24
<212> TYPE: DNA
<213> ORGANISM: artificial
<220> FEATURE:
<223> OTHER INFORMATION: Oligonucleotide

<400> SEQUENCE: 9
gggttactgg gtgccgcaat atcc                                            24

<210> SEQ ID NO 10
<211> LENGTH: 27
<212> TYPE: DNA
<213> ORGANISM: artificial
<220> FEATURE:
<223> OTHER INFORMATION: Oligonucleotide

<400> SEQUENCE: 10
cctcaatcca gcattcgcca ttatacg                                         27

<210> SEQ ID NO 11
<211> LENGTH: 796
<212> TYPE: DNA
<213> ORGANISM: artificial
<220> FEATURE:
<223> OTHER INFORMATION: Construct

<400> SEQUENCE: 11
gctgccgtgg ttcaagtcgc gactaataaa aataatcagg ttgccatgat tcaatgtaca      60
cctttctcac attcgtctcc ggcatgaaaa cgatgcactc tttctttatc gctttcacta     120
cacattttat cctcgcatgg atgttttata aaaacatga ttgacatcat gttgcatata      180
ggttaaacaa aacaagtggc gttatctttt tccggattgt cttcttgtat gatatataag     240
ttttcctcga tgaataaagt aaaatgttat gttttattta cggcgttact atcctctcta     300
tgtgcatacg gagctcccca gtctattaca gaactatgtt cggaatatcg caacacacaa     360
atatatacga taaatgacaa gatactatca tatacggaat cgatggcagg caaaagagaa     420
atggttatca ttcatttaa gagcggcgca acatttcagg tcgaagtccc gggcagtcaa      480
catatagact cccaaaaaaa agccattgaa aggatgaagg acacattaag aatcacatat     540
ctgaccgaga ccaaaattga taaattatgt gtatggaata ataaaacccc caattcaatt     600
gcggcaatca gtatggaaaa cgggccgggg cccaattctt ctaactactg ctgtgaactt     660
tgttgtaatt ttgcctgtac aggatgttac tagtttgctt taaaagcatg tctaatgcta     720
```

```
ggaacctata taacaactac tgtacttata ctaatgagcc ttatgctgca tttgaaaagg    780
cggtagagga tgcaat                                                    796
```

```
<210> SEQ ID NO 12
<211> LENGTH: 147
<212> TYPE: PRT
<213> ORGANISM: artificial
<220> FEATURE:
<223> OTHER INFORMATION: Construct

<400> SEQUENCE: 12
```

```
Met Asn Lys Val Lys Cys Tyr Val Leu Phe Thr Ala Leu Leu Ser Ser
1               5                   10                  15

Leu Cys Ala Tyr Gly Ala Pro Gln Ser Ile Thr Glu Leu Cys Ser Glu
            20                  25                  30

Tyr Arg Asn Thr Gln Ile Tyr Thr Ile Asn Asp Lys Ile Leu Ser Tyr
        35                  40                  45

Thr Glu Ser Met Ala Gly Lys Arg Glu Met Val Ile Ile Thr Phe Lys
    50                  55                  60

Ser Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Thr
                85                  90                  95

Tyr Leu Thr Glu Thr Lys Ile Asp Lys Leu Cys Val Trp Asn Asn Lys
            100                 105                 110

Thr Pro Asn Ser Ile Ala Ala Ile Ser Met Glu Asn Gly Pro Gly Pro
        115                 120                 125

Asn Ser Ser Asn Tyr Cys Cys Glu Leu Cys Cys Asn Phe Ala Cys Thr
    130                 135                 140

Gly Cys Tyr
145
```

```
<210> SEQ ID NO 13
<211> LENGTH: 799
<212> TYPE: DNA
<213> ORGANISM: artificial
<220> FEATURE:
<223> OTHER INFORMATION: Construct

<400> SEQUENCE: 13
gctgccgtgg ttcaagtcgc gactaataaa aataatcagg ttgccatgat tcaatgtaca     60
cctttctcac attcgtctcc ggcatgaaaa cgatgcactc tttctttatc gctttcacta    120
cacattttat cctcgcatgg atgttttata aaaaacatga ttgacatcat gttgcatata    180
ggttaaacaa aacaagtggc gttatctttt tccggattgt cttcttgtat gatatataag    240
ttttcctcga tgaataaagt aaaatgttat gtttttattta cggcgttact atcctctcta    300
tgtgcatacg gagctcccca gtctattaca gaactatgtt cggaatatcg caacacacaa    360
atatatacga taaatgacaa gatactatca tatacggaat cgatggcagg caaaagagaa    420
atggttatca ttacatttaa gagcggcgca catttcagg tcgaagtccc gggcagtcaa     480
catatagact cccaaaaaaa agccattgaa aggatgaagg acacattaag aatcacatat    540
ctgaccgaga ccaaaattga taattatgt gtatggaata ataaaccccc caattcaatt    600
gcggcaatca gtatggaaaa cggcggaggt ggctccaatt cttctaacta ctgctgtgaa    660
ctttgttgta atggcgcctg tacaggatgt tactagtttg ctttaaaagc atgtctaatg    720
ctaggaacct atataacaac tactgtactt atactaatga gccttatgct gcatttgaaa    780
```
aggcggtaga ggatgcaat                                                    799

<210> SEQ ID NO 14
<211> LENGTH: 148
<212> TYPE: PRT
<213> ORGANISM: artificial
<220> FEATURE:
<223> OTHER INFORMATION: Construct

<400> SEQUENCE: 14

Met Asn Lys Val Lys Cys Tyr Val Leu Phe Thr Ala Leu Leu Ser Ser
1               5                   10                  15

Leu Cys Ala Tyr Gly Ala Pro Gln Ser Ile Thr Glu Leu Cys Ser Glu
            20                  25                  30

Tyr Arg Asn Thr Gln Ile Tyr Thr Ile Asn Asp Lys Ile Leu Ser Tyr
        35                  40                  45

Thr Glu Ser Met Ala Gly Lys Arg Glu Met Val Ile Ile Thr Phe Lys
    50                  55                  60

Ser Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Thr
                85                  90                  95

Tyr Leu Thr Glu Thr Lys Ile Asp Lys Leu Cys Val Trp Asn Asn Lys
            100                 105                 110

Thr Pro Asn Ser Ile Ala Ala Ile Ser Met Glu Asn Gly Gly Gly Gly
        115                 120                 125

Ser Asn Ser Ser Asn Tyr Cys Cys Glu Leu Cys Cys Asn Gly Ala Cys
    130                 135                 140

Thr Gly Cys Tyr
145

<210> SEQ ID NO 15
<211> LENGTH: 799
<212> TYPE: DNA
<213> ORGANISM: artificial
<220> FEATURE:
<223> OTHER INFORMATION: Construct

<400> SEQUENCE: 15
gctgccgtgg ttcaagtcgc gactaataaa aataatcagg ttgccatgat tcaatgtaca      60
cctttctcac attcgtctcc ggcatgaaaa cgatgcactc tttctttatc gctttcacta     120
cacattttat cctcgcatgg atgttttata aaaaacatga ttgacatcat gttgcatata     180
ggttaaacaa acaagtggc gttatctttt tccggattgt cttcttgtat gatatataag      240
ttttcctcga tgaataaagt aaaatgttat gttttattta cggcgttact atcctctcta     300
tgtgcatacg gagctcccca gtctattaca gaactatgtt cggaatatcg caacacacaa     360 atatatcga taaatgacaa gatactatca tatacggaat cgatggcagg caaaagagaa      420
atggttatca ttacatttaa gagcggcgca catttcagg tcgaagtccc gggcagtcaa      480
catatagact cccaaaaaaa agccattgaa aggatgaagg acacattaag aatcacatat     540
ctgaccgaga ccaaaattga taattatgt gtatggaata taaaacccc caattcaatt      600 gcggcaatca gtatggaaaa cggcggaggt ggctccaatt cttctaacta ctgctgtgaa     660 cttgtgtc gccctgcctg tacaggatgt tactagtttg ctttaaaagc atgtctaatg       720
ctaggaacct atataacaac tactgtactt atactaatga gccttatgct gcatttgaaa     780

```
aggcggtaga ggatgcaat                                                  799
```

<210> SEQ ID NO 16
<211> LENGTH: 148
<212> TYPE: PRT
<213> ORGANISM: artificial
<220> FEATURE:
<223> OTHER INFORMATION: Construct

<400> SEQUENCE: 16

```
Met Asn Lys Val Lys Cys Tyr Val Leu Phe Thr Ala Leu Leu Ser Ser
1               5                   10                  15

Leu Cys Ala Tyr Gly Ala Pro Gln Ser Ile Thr Glu Leu Cys Ser Glu
            20                  25                  30

Tyr Arg Asn Thr Gln Ile Tyr Thr Ile Asn Asp Lys Ile Leu Ser Tyr
        35                  40                  45

Thr Glu Ser Met Ala Gly Lys Arg Glu Met Val Ile Ile Thr Phe Lys
    50                  55                  60

Ser Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Thr
                85                  90                  95

Tyr Leu Thr Glu Thr Lys Ile Asp Lys Leu Cys Val Trp Asn Asn Lys
            100                 105                 110

Thr Pro Asn Ser Ile Ala Ala Ile Ser Met Glu Asn Gly Gly Gly
        115                 120                 125

Ser Asn Ser Ser Asn Tyr Cys Cys Glu Leu Cys Cys Arg Pro Ala Cys
130                 135                 140

Thr Gly Cys Tyr
145
```

<210> SEQ ID NO 17
<211> LENGTH: 799
<212> TYPE: DNA
<213> ORGANISM: artificial
<220> FEATURE:
<223> OTHER INFORMATION: Construct

<400> SEQUENCE: 17

```
gctgccgtgg ttcaagtcgc gactaataaa aataatcagg ttgccatgat tcaatgtaca    60
cctttctcac attcgtctcc ggcatgaaaa cgatgcactc tttctttatc gctttcacta   120
cacattttat cctcgcatgg atgttttata aaaaacatga ttgacatcat gttgcatata   180
ggttaaacaa aacaagtggc gttatctttt tccggattgt cttcttgtat gatatataag   240
ttttcctcga tgaataaagt aaaatgttat gtttttattta cggcgttact atcctctcta   300
tgtgcatacg gagctcccca gtctattaca gaactatgtt cggaatatcg caacacacaa   360
atatatacga taaatgacaa gatactatca tatacggaat cgatggcagg caaaagagaa   420
atggttatca ttacatttaa gagcggcgca acatttcagg tcgaagtccc gggcagtcaa   480
catatagact cccaaaaaaa agccattgaa aggatgaagg acacattaag aatcacatat   540
ctgaccgaga ccaaaattga taaattatgt gtatggaata taaaaccccc caattcaatt   600
gcggcaatca gtatggaaaa cggcggaggt ggctccaatt cttctaacta ctgctgtgaa   660
ctttgttgta aacctgcctg tacaggatgt tactagtttg ctttaaaagc atgtctaatg   720
ctaggaacct ataacaac tactgtactt atactaatga gccttatgct gcatttgaaa   780
aggcggtaga ggatgcaat                                                799
```

```
<210> SEQ ID NO 18
<211> LENGTH: 148
<212> TYPE: PRT
<213> ORGANISM: artificial
<220> FEATURE:
<223> OTHER INFORMATION: Construct

<400> SEQUENCE: 18

Met Asn Lys Val Lys Cys Tyr Val Leu Phe Thr Ala Leu Leu Ser Ser
1               5                   10                  15

Leu Cys Ala Tyr Gly Ala Pro Gln Ser Ile Thr Glu Leu Cys Ser Glu
            20                  25                  30

Tyr Arg Asn Thr Gln Ile Tyr Thr Ile Asn Asp Lys Ile Leu Ser Tyr
        35                  40                  45

Thr Glu Ser Met Ala Gly Lys Arg Glu Met Val Ile Ile Thr Phe Lys
    50                  55                  60

Ser Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Thr
                85                  90                  95

Tyr Leu Thr Glu Thr Lys Ile Asp Lys Leu Cys Val Trp Asn Asn Lys
            100                 105                 110

Thr Pro Asn Ser Ile Ala Ala Ile Ser Met Glu Asn Gly Gly Gly Gly
        115                 120                 125

Ser Asn Ser Ser Asn Tyr Cys Cys Glu Leu Cys Cys Lys Pro Ala Cys
    130                 135                 140

Thr Gly Cys Tyr
145

<210> SEQ ID NO 19
<211> LENGTH: 20
<212> TYPE: DNA
<213> ORGANISM: artificial
<220> FEATURE:
<223> OTHER INFORMATION: Primer

<400> SEQUENCE: 19
gtaagcacca caaccactgg                                               20

<210> SEQ ID NO 20
<211> LENGTH: 22
<212> TYPE: DNA
<213> ORGANISM: artificial
<220> FEATURE:
<223> OTHER INFORMATION: Primer

<400> SEQUENCE: 20
ccagcaatct gactggctgt cg                                            22

<210> SEQ ID NO 21
<211> LENGTH: 77
<212> TYPE: DNA
<213> ORGANISM: artificial
<220> FEATURE:
<223> OTHER INFORMATION: Construct

<400> SEQUENCE: 21
gccaaaatat tggcttccac tgagcttgga gacaatacta tccaagccat atgaatatcc    60
tccttagttc ctaatcc                                                  77
```

<210> SEQ ID NO 22
<211> LENGTH: 65
<212> TYPE: DNA
<213> ORGANISM: artificial
<220> FEATURE:
<223> OTHER INFORMATION: Construct

<400> SEQUENCE: 22

| | |
|---|---|
| gtattaattg atttgtcgct tgggatgctt ctttagatac ttggggtgta ggctggagct | 60 |
| gcttc | 65 |

<210> SEQ ID NO 23
<211> LENGTH: 2854
<212> TYPE: DNA
<213> ORGANISM: artificial
<220> FEATURE:
<223> OTHER INFORMATION: Gene

<400> SEQUENCE: 23

| | |
|---|---|
| atgcataatg taagcaccac aaccactggt tttcctcttg ccaaaatatt ggcttccact | 60 |
| gagcttggag acaatactat ccaagctgca aatgatgcag ctaacaaatt attttctctt | 120 |
| acaattgctg atcttactgc taaccaaaat attaatacaa ctaatgcaca ctcaacttca | 180 |
| aatatattaa tccctgaact taaagcacca aagtcattaa atgcaagttc ccaactaacg | 240 |
| cttttaattg gaaaccttat tcaaatactc ggtgaaaaat ctttaactgc attaacaaat | 300 |
| aaaattactg cttggaagtc ccagcaacag gcaagacagc aaaaaaacct agaattctcc | 360 |
| gataaaatta cactcttct atctgaaact gaaggactaa ccagagacta tgaaaaacaa | 420 |
| attaataaac taaaaaacgc agattctaaa ataaagacc tagaaaataa aattaaccaa | 480 |
| attcaaacaa gattatccga actcgaccca gagtcaccag aaaagaaaaa attaagccgg | 540 |
| gaagaaatac aactcactat caaaaaagac gcagcagtta agacaggac attgattgag | 600 |
| cagaaaaccc tgtcaattca tagcaaactt acagataaat caatgcaact cgaaaaagaa | 660 |
| atagactctt tttctgcatt tcaaacacag gcatctgctg aacagctatc aacccagcag | 720 |
| aaatcattaa ccggacttgc cagtgttact caattgatgg caacctttat tcaactagtt | 780 |
| ggaaaaaata atgaagaatc tttaaaaat gatctggctc tattccagtc tctccaagaa | 840 |
| tcaagaaaaa ctgaaatgga gagaaaatct gatgagtatg ctgctgaagt acgtaaagca | 900 |
| gaagaactca acagagtaat gggttgtgtt gggaaaatac ttggggcact tttaactatc | 960 |
| gttagtgttg ttgcagcagc ttttctgga ggagcctctc tagcactggc agctgttggt | 1020 |
| ttagctctta tggttacgga tgctatagta caagcagcga ccggcaattc cttcatggaa | 1080 |
| caagccctga tccgatcat gaaagcagtc attgaaccct aatcaaaact cctttcagat | 1140 |
| gcatttacaa aaatgctcga aggcttgggc gtcgactcga aaaagccaa atgattggc | 1200 |
| tctattctgg gggcaatcgc aggcgctctt gtcctagttg cagcagtcgt tctcgtagcc | 1260 |
| actgttggta acaggcagc agcaaaactt gcagaaaata ttggcaaaat aataggtaaa | 1320 |
| accctcacag accttatacc aaagtttctc aagaattttt cttctcaact ggacgattta | 1380 |
| atcactaatg ctgttgccag attaaataaa tttcttggtg cagcgggtga tgaagtaata | 1440 |
| tccaaacaaa ttatttccac ccatttaaac caagcagttt tattaggaga agtgttaac | 1500 |
| tctgccacac aagcgggagg aagtgtcgct tctgctgttt tccagaacag cgcgtcgaca | 1560 |
| aatctagcag acctgacatt atcgaaatat caagttgaac aactgtcaaa atatatcagt | 1620 |
| gaagcaatag aaaaattcgg ccaattgcag gaagtaattg cagatctatt agcctcaatg | 1680 |

```
tccaactctc aggctaatag aactgatgtt gcaaaagcaa ttttgcaaca aactactgct    1740
tgatacaaat aaggagaatg ttatggaaat tcaaaacaca aaaccaaccc agattttata    1800
tacagatata tccacaaaac aaactcaaag ttcttccgaa acacaaaaat cacaaaatta    1860
tcagcagatt gcagcgcata ttccacttaa tgtcggtaaa aatcccgtat taacaaccac    1920
attaaatgat gatcaacttt taaagttatc agagcaggtt cagcatgatt cagaaatcat    1980
tgctcgcctt actgacaaaa agatgaaaga tcgttcagag atgagtcaca cccttactcc    2040
agagaacact ctggatattt ccagtctttc ttctaatgct gtttctttaa ttattagtgt    2100
agccgttcta ctttctgctc tccgcactgc agaaactaaa ttgggctctc aattgtcatt    2160
gattgcgttc gatgctacaa aatcagctgc agagaacatt gttcggcaag cctggcagc    2220 cctatcatca agcattactg gagcagtcac acaagtaggt ataacgggta tcggtgccaa    2280
aaaaacgcat tcagggatta gcgaccaaaa aggagcctta agaaagaacc ttgccactgc    2340
tcaatctctt gaaaagagc ttgcaggttc taaattaggg ttaaataaac aaatagatac    2400
aaatatcacc tcaccacaaa ctaactctag cacaaaattt ttaggtaaaa ataaactggc    2460
gccagataat atatccctgt caactgaaca taaaacttct cttagttctc ccgatatttc    2520
tttgcaggat aaaattgaca cccagagaag aacttacgag ctcaataccc tttctgcgca    2580
gcaaaaacaa aacattggcc gtgcaacaat ggaaacatca gccgttgctg gtaatatatc    2640
cacatcagga gggcgttatg catctgctct tgaagaagaa gaacaactaa tcagtcaggc    2700
cagcagtaaa caagcagagg aagcatccca agtatctaaa gaagcatccc aagcgacaaa    2760
tcaattaata caaaaattat tgaatataat tgacagcatc aaccaatcaa agaattcgac    2820
agccagtcag attgctggta acattcgagc ttaa    2854

<210> SEQ ID NO 24
<211> LENGTH: 938
<212> TYPE: DNA
<213> ORGANISM: artificial
<220> FEATURE:
<223> OTHER INFORMATION: Gene

<400> SEQUENCE: 24
aagtaaataa aacgttaatc acaagtttgt aatcgctttc atctcactat gaaaaatgcg     60
gctacggtta tggattttcc tgctctgtat accgtcttaa aactggcgaa aaaggaaaat    120
gaagacgaaa acaagcaaag acattcggcg cgagttggct ataatacttg gcacttgttt    180
gccacatatt tttaaaggaa acagacatga gcttactcaa cgtccctgcg ggtaaagatc    240
tgccggaaga catctacgtt gttattgaga tcccggctaa cgcagatccg atcaaatacg    300
aaatcgacaa agagagcggc gcactgttcg ttgaccgctt catgtccacc gcgatgttct    360
atccgtgcaa ctacggttac atcaaccaca ccctgtctct ggacggtgac ccggttgacg    420
tactggtccc gactccgtac ccgctgcagc ctggttctgt gatccgttgc cgtccggttg    480
ccgttctgaa aatgaccgac gaagccggtg aagatgcaaa actggttgcg gttccgcaca    540
gcaagctgag caaagaatac gatcacatta aagacgtaaa cgatctgcct gaactgctga    600
aagcgcaaat cgctcacttc ttcgagcact acaaagacct cgaaaaaggc aagtgggtga    660
aagttgaagg ttgggaaaac gcagaagccg ctaaagctga atcgttgct tccttcgagc    720 gcgcaaagaa taaataagtt cttctagcgc aataaccctg aacgccgggc ttcggttagt    780
aagggttttt ttatgcccgc gataaataaa ctctctattc caccatcatt attctcagcg    840
```

-continued

```
gttgcaaggc ttgaacggta agaacaagca aacccgacca ccattttgct gttcatagcc    900
acttgctgga agttagccga cctcactcat actcaccg                            938
```

<210> SEQ ID NO 25
<211> LENGTH: 90
<212> TYPE: DNA
<213> ORGANISM: artificial
<220> FEATURE:
<223> OTHER INFORMATION: Primer

<400> SEQUENCE: 25

```
ttattattgg tgaaaagatg ttcgcgaaaa aactatagac aattcgttat gtaacggatt    60
gcgttacatc gtgtaggctg gagctgcttc                                     90
```

<210> SEQ ID NO 26
<211> LENGTH: 100
<212> TYPE: DNA
<213> ORGANISM: artificial
<220> FEATURE:
<223> OTHER INFORMATION: Primer

<400> SEQUENCE: 26

```
tccatatctg caatcgcata aaaaactctg ctggcgttca caaatgtgca ggggtaaaac    60
gggggcacgc catatgaata cctccttag ttcctaatcc                          100
```

<210> SEQ ID NO 27
<211> LENGTH: 22
<212> TYPE: DNA
<213> ORGANISM: artificial
<220> FEATURE:
<223> OTHER INFORMATION: Primer

<400> SEQUENCE: 27

```
catagggttg tcctcgtcgg gg                                             22
```

<210> SEQ ID NO 28
<211> LENGTH: 22
<212> TYPE: DNA
<213> ORGANISM: artificial
<220> FEATURE:
<223> OTHER INFORMATION: Primer

<400> SEQUENCE: 28

```
gttttatgcg atgtatctcg cg                                             22
```

<210> SEQ ID NO 29
<211> LENGTH: 5
<212> TYPE: PRT
<213> ORGANISM: artificial
<220> FEATURE:
<223> OTHER INFORMATION: Linker

<400> SEQUENCE: 29

```
Gly Gly Gly Gly Ser
1               5
```